US006878255B1

(12) United States Patent
Wang et al.

(10) Patent No.: US 6,878,255 B1
(45) Date of Patent: Apr. 12, 2005

(54) MICROFLUIDIC DEVICES WITH THICK-FILM ELECTROCHEMICAL DETECTION

(75) Inventors: Joseph Wang, Las Cruces, NM (US); Baomin Tian, Las Cruces, NM (US); Eskil Sahlin, Pittsburgh, PA (US)

(73) Assignee: Arrowhead Center, Inc., Las Cruces, NM (US)

( * ) Notice: Subject to any disclaimer, the term of this patent is extended or adjusted under 35 U.S.C. 154(b) by 468 days.

(21) Appl. No.: 09/705,100

(22) Filed: Nov. 2, 2000

Related U.S. Application Data

(60) Provisional application No. 60/163,852, filed on Nov. 5, 1999.

(51) Int. Cl.[7] ..................... G01N 27/26; G01N 27/447; G01N 27/453

(52) U.S. Cl. ..................... 204/452; 204/451; 204/455; 204/601; 204/603; 204/605; 435/6

(58) Field of Search ............................... 204/451, 452, 204/455, 601, 603, 605; 435/6

(56) References Cited

U.S. PATENT DOCUMENTS

| | | | |
|---|---|---|---|
| 4,908,112 A | | 3/1990 | Pace |
| 5,846,727 A | | 12/1998 | Soper et al. |
| 5,858,195 A | | 1/1999 | Ramsey |
| 5,872,010 A | * | 2/1999 | Karger et al. ............... 436/173 |
| 5,904,824 A | | 5/1999 | Oh |
| 5,906,723 A | | 5/1999 | Mathies |
| 6,045,676 A | | 4/2000 | Mathies et al. |
| 6,063,259 A | | 5/2000 | Wang et al. |
| 6,068,752 A | | 5/2000 | Dubrow et al. |
| 6,103,199 A | | 8/2000 | Bjornson et al. |
| 6,110,343 A | * | 8/2000 | Ramsey et al. ............. 204/601 |
| 6,207,031 B1 | * | 3/2001 | Adourian et al. ........... 204/451 |
| 6,251,343 B1 | * | 6/2001 | Dubrow et al. ............. 422/102 |
| 6,274,089 B1 | * | 8/2001 | Chow et al. ................ 422/101 |

FOREIGN PATENT DOCUMENTS

WO    WO 98/09161 A1    3/1998

OTHER PUBLICATIONS

Wang, J., et al., "Electrochemical Activation of Screen-Printed Carbon Strips," Analyst, vol. 121, pp 345–350 (Mar. 1996).

Wang, J., et al., "Performance of Screen–Printed Carbon Electrodes Fabricated from Different Carbon Inks," Electrochimica Acta, vol. 43, No. 23, pp 34359–3465 (1998).

Wang, J., et al., "Integrated Electrophoresis Chips/Amperometric Detection with Sputtered Gold Working Electrodes," Anal. Chem., vol. 71, No. 17, pp 3901–3904 (1999).

Wang, J., et al., "Capillary Electrophoresis Chips with Thick–Film Amperometric Detectors: Separation and Detection of Hydrazine Compounds," Electroanalysis 2000, vol. 12, No. 9, pp 691–694 (1999).

Wang, J., et al., "Capillary Electrophoresis Chips with Thick–Film Amperometric Detectors: Separation and Detection of Phenolic Compounds," Analytica Chimica Acta, vol. 416, pp 9–14 (2000).

(Continued)

Primary Examiner—Nam Nguyen
Assistant Examiner—Brian L. Mutschler
(74) Attorney, Agent, or Firm—Peacock Myers & Adams PC; Stephen A. Slusher

(57) ABSTRACT

An apparatus for conducting a microfluidic process and analysis, including at least one elongated microfluidic channel, fluidic transport means for transport of fluids through the microfluidic channel, and at least one thick-film electrode in fluidic connection with the outlet end of the microfluidic channel. The present invention includes an integrated on-chip combination reaction, separation and thick-film electrochemical detection microsystem, for use in detection of a wide range of analytes, and methods for the use thereof.

82 Claims, 25 Drawing Sheets

OTHER PUBLICATIONS

Wang, J., et al., "Micromachined Electrophoresis Chips with Thick–Film Electrochemical Detectors," Analytical Chem., vol. 71, No. 23, pp 5436–5440 (Dec. 1, 1999).

Wang, J., et al., "Microfabricated Electrophoresis Chips for Simultaneous Bioassays of Glucose, Uric Acid, Ascorbic Acid and Acetaminophen," Analytical Chem., vol. 72, No. 11, pp 2514–2518 (Jun. 1, 2000).

Wang, J., Textbook "Analytical Electrochemistry" Wiley–VCH, A. John Wiley & Sons, Inc., New York, Second Edition (2000) copy of table of contents provided only.

Woolley, A.T., et al., "Capillary Electrophoresis Chips with Integrated Electrochemical Detection," Anal. Chem., vol. 70, pp 684–688 (1998).

Zhong, M., t al., "Integrated On–Capillary Electrochemical Detector for Capillary Electrophoresis," Anal. Chem., vol. 68, pp 2488–2493 (1996).

Curry Jr., P.D., et al., "Electrochemical Detection for Capillary Electrophoresis," Electroanalysis, vol. 3, pp 587–596 (1991).

Freemantle, M., "Downsizing Chemistry," C&EN pp 27–35 (Feb. 22, 1999).

Gavin, P.F., et al., "Characterization of Electrochemical array Detection for continuous Channel Electrophoretic Separations in Micrometer and Submicrometer Channels," Anal. Chem., vol. 69, pp 3838–3845 (1997).

Gunasingham, H., et al., "Wall–Jet Eelctrode in Continuous Monitoring Voltammetry," Anal. Chem. vol. 55, pp 1409–1414 (1983).

Hadd, A.G., et al., "Microchip Device for Performing Enzyme Assays," Anal. Chem, vol. j6, pp 3407–3412 (1997).

Hart, J.P., et al., "Screen–Printed Voltammetric and Amperometric Electrochemical Sensors for Decentralized Testing," Electroanalysis, vol. 6, pp 617–624 (1994).

Hilmi, A., et al., "Development of Electorkinetic Capillary Electrophoresis Equipped with Amprometric Detection for Analysis of Explosive Compounds," Anal. Chem., vol. 71, pp 873–878 (1999).

Holland, L.A., et al., "Capillary Electrophoresis Coupled to Electrochemical Detection: A Review of Recent Advances," Analytical Communications vol. 35, pp 1H–4H (Feb. 1998).

Kirk, Julienne K., et al., "Important Features of Blood Blucose Meters," Journal of Amer. Pharm Assn, vol. 38, No. 2, PP 210–219 (Mar./Apr. 1998).

Kovacs, G.T.A., et al., "Silicon Micromachining Sensors to Systems" Anal. Chem., pp 407A–412A Jul. 1, 1996).

Rippeth, J.J., et al., "Flow–Injection Detector Incorporating a Screen–Printed Dispensable Amperometric Biosensor for Monitoring Organophosphate Pesticides," Analyst, vol. 122, pp 1425–1429 (Nov. 1997).

Henry, C.S., et al., "Ceramic Microchips for Electrophoresis–Electrochemistry," *Anal. Commun.*, vol. 36, pp 305–307 (1999).

Hilmi, A., et al., "Electrochemical Detectors Prepared by Electroless Deposition for Microfabricated Electrophoresis Chips," *Analytical Chemistry*, vol. 72, No. 19, pp 4577–4682 (Oct. 1, 2000).

Rossler, J.S., et al., "Microchannel Networks for Electrophoretic Separations," *Electrophoresis*, vol. 20, pp 727–731 (1999).

* cited by examiner

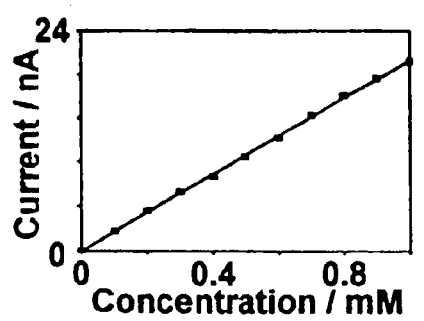
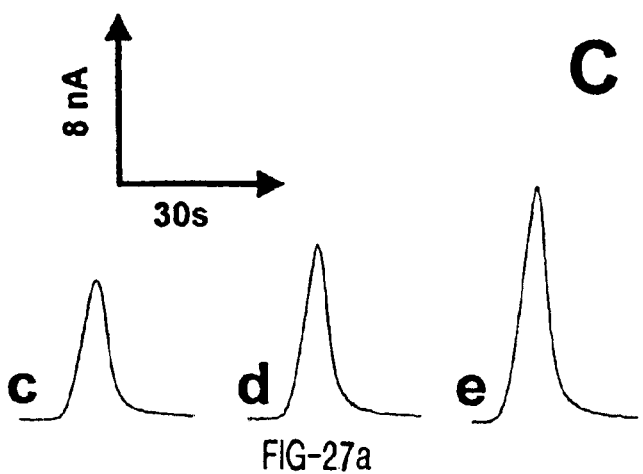
FIG-27a
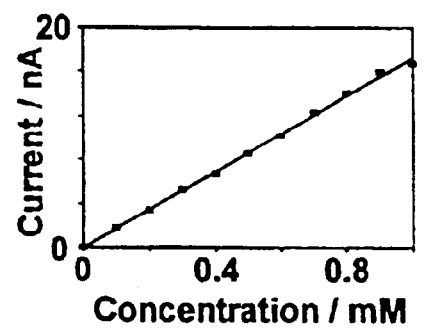
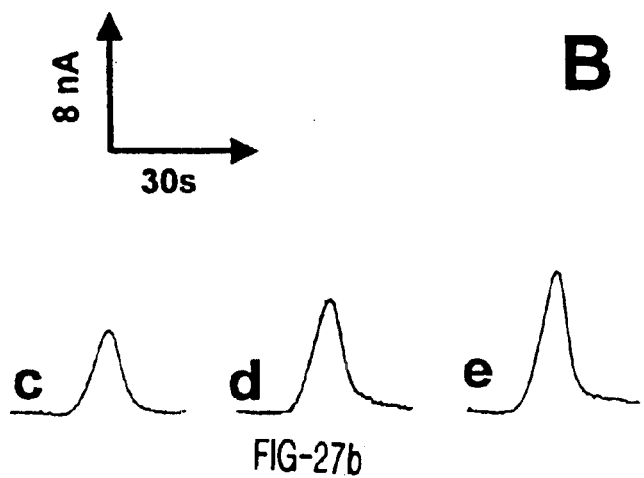
FIG-27b
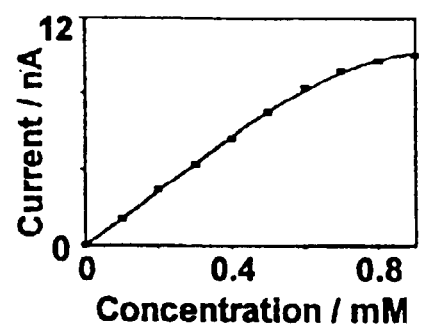
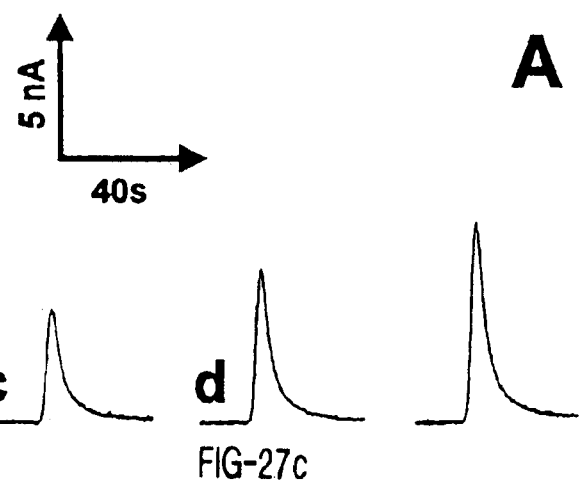
FIG-27c

FIG-3.3

| Multiple | Multiple | Mixed oxidase/ | Mixed oxidase/ |
| Oxidases | Dehydrogendases | dehydrogenase | dehydrogenase |

MICROFLUIDIC DEVICES WITH THICK-FILM ELECTROCHEMICAL DETECTION

CROSS-REFERENCE TO RELATED APPLICATIONS

This application claims the benefit of the filing of U.S. Provisional Patent Application Ser. No. 60/163,852, entitled Micromachined Electrophoresis Chips with Integrated Thick-Film Electrochemical Detectors, filed on Nov. 5, 1999, and the specification thereof is incorporated herein by reference.

GOVERNMENT RIGHTS

The U.S. Government has a paid-up license in certain aspects of this invention and the right in limited circumstances to require the patent owner to license others on reasonable terms as provided for by the terms of contract no. AV-8698 with Sandia National Laboratory on behalf of the United States Department of Energy.

COPYRIGHTED MATERIAL

A portion of the disclosure of this patent document contains material that is subject to copyright protection. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention (Technical Field)

The present invention relates to electrochemical detection of analytes using thick-film electrodes, including screen-printed thick-film electrodes, in microfluidic devices, including separation devices such as capillary electrophoresis microsystems.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Microscale separation devices, particularly chip-based, micromachined capillary electrophoresis (CE) systems, have witnessed an explosive growth in recent years. These miniaturized devices present the ability to shrink conventional "bench-top" separation systems while providing major advantages in speed, cost, portability, and solvent/sample consumption. As the field of chip-based separation microsystems continues its rapid growth, there is an urgent need for developing compatible detection modes and systems. Much of the work on CE microchips uses laser-fluorescence detection. Yet, such detection requires a large and expensive supporting optical system, and is limited to analytes that fluoresce or are amenable to derivatization with a fluorophore. Microscale CE systems are described generally in, among others, U.S. Pat. Nos. 5,904,824, 6,068,752 and 6,103,199.

Electrochemical detection is used in a wide variety of areas. Such detection offers remarkable sensitivity (comparable to that of fluorescence), tunable selectivity, and low-volume requirements. Electrochemical detection is generally described in J. Wang, *Analytical Electrochemistry*, $2^{nd}$ Ed., Wiley-VHC, New York, 2000. Electrochemical detection has proven to be extremely useful for conventional CE systems based on fused-silica capillaries, but has rarely been used for planar micromachined CE chips. The major challenges for such integration are similar to those of conventional CE systems, namely isolation of the working electrode from the high separation voltage and its proper alignment with the capillary. The use of integral lithographically-fabricated thin-film electrodes and separation channels, with the thin-film electrode located inside the exit of the channel, have been described (U.S. Pat. Nos. 6,045,676 and 5,906,723); Gavin and Ewing (*Anal. Chem.* 1997, 69, 3838) developed a thin-film microfabricated electrochemical array detector for planar CE chips, while certain of the inventors herein have described an on-chip thin-film detector based on sputtering the working electrode directly onto the channel outlet (*Anal. Chem.* 1999, 71, 3901).

Microscale fluidic devices coupled with electrochemical detection means are applicable to a wide variety of environmental, research, industrial and medical applications, among others. For example, such devices could be used in operating rooms, emergency departments, intensive care units, ambulances, clinics and the like for rapidly and reliably monitoring a wide range of analytes. While CE is the primary electrically driven separation modality used in microfluidic applications, other separation modalities have been described for microscale fluidic devices, including pump and other mechanical transport devices.

SUMMARY OF THE INVENTION (DISCLOSURE OF THE INVENTION)

This invention provides an apparatus for conducting a microfluidic process and analysis, which apparatus includes a first substrate, at least one elongated separation channel in the first substrate, the separation channel having an inlet end and an outlet end, a fluidic transport for transport of fluids through the separation channel, a second substrate and at least one thick-film electrode on the second substrate, the thick-film electrode being in fluidic connection with the outlet end of the separation channel. In this apparatus, the fluidic transport can be a conductive system in fluidic connection with each end of the separation channel for application of a separation voltage, which conductive system can include electrodes. The apparatus can also include a high-voltage power supply for application of voltage to the conductive system. In the apparatus, the fluidic transport can include electrokinetic fluid transport, and may also include other forms of fluidic transport, such as electrical, mechanical, centrifugal, magnetic, pneumatic, pressure-activated, or vacuum-activated fluid transport.

The first substrate of the apparatus can include a fused-silica, silica-based, polymer, plastic or elastomer material, and the second substrate can include a ceramic, polymeric or plastic material.

The apparatus can include at least one reference electrode in fluidic connection with the thick-film electrode and also an electrical contact to the thick-film electrode. The thick-film electrode may be a screen-printed electrode. The apparatus can include an analyte analysis system in electrical contact with the electrical contact to the thick-film electrode. Thus the apparatus includes an analyte analysis system for analyzing an analyte at the thick-film electrode. The analyte analysis system can be an amperometric detection system in one embodiment, and may be either a fixed potential or potential-step amperometric detection system. The analyte analysis system can also include a stripping potentiometry system or a voltammetric detection system.

The separation channel in the apparatus can have an average bore diameter of from about 1 $\mu$m to about 300 $\mu$m, and preferably from about 20 $\mu$m to about 120 $\mu$m. The separation channel can also include separation media within the channel. The thick-film electrode has a thickness of from about 1 $\mu$m to about 100 $\mu$m, and preferably between about 8 $\mu$m and 30 $\mu$m.

In one embodiment, the first substrate that includes at least one elongated separation channel is detachable from the second substrate that includes at least one thick-film electrode. In this embodiment, the first substrate can be affixed to the second substrate such that the distance between the thick-film electrode and the outlet end of the separation channel is fixed. The distance between the thick-film electrode and the outlet end of the separation channel is from about 1 $\mu$m to about 500 $\mu$m, and preferably between about 50 $\mu$m and about 100 $\mu$m.

The thick-film electrode can be a carbon ink electrode, and can also include other constituents. Thus the thick-film electrode can include a metal conducting coating, and can generally include metals, inorganic dopants, organic dopants, nucleic acids, catalytic surface modifiers, enzymatic surface modifiers or permselective film coatings.

In the apparatus, there can be provided at least one cavity in fluidic connection with the inlet end of the separation channel. The apparatus can also include one or more buffer cavities and sample cavities in fluidic connection with the inlet end of the separation channel. One or more reaction cavity in fluidic connection with the inlet end of the separation channel can also be provided. The apparatus can include a plurality of separation channels with the inlet ends thereof in fluidic connection with the cavity. There can also be at least one cavity in fluidic connection with the outlet end of the separation channel. Finally, the apparatus can include a plurality of separation channels and a plurality of thick-film electrodes.

In one embodiment of the apparatus, both the first substrate and the second substrate are substantially planar, and the second substrate is at an angle to the first substrate. In this embodiment, the second substrate can be perpendicular to the first substrate. In another embodiment, the first substrate and the second substrate can be substantially planar and parallel to each other. In this embodiment, the second substrate can form a seal for at least a portion of the separation channel of the first substrate.

The invention also includes a method for detecting an analyte, in which are included the steps of introducing the analyte in the inlet end of a microfluidic channel having an inlet end and an outlet end; transporting the analyte in a fluid solution through the microfluidic channel to the outlet end; contacting the solution containing the analyte with a thick-film electrode in fluidic connection with the outlet end of the microfluidic channel; providing electrical contact to the thick-film electrode; and analyzing the analyte at the thick-film electrode by electrochemical detection. This method can include the additional step of providing electrical contact to at least one counter electrode in fluidic contact with the thick-film electrode, and also the optional steps of providing at least one reactant for the analyte and mixing the at least one reactant and the analyte prior to introducing the analyte in the inlet end of the microfluidic channel.

In this method, the microfluidic channel can include a microfluidic separation channel. Transporting the analyte in a fluid solution through the microfluidic channel is by electrokinetic fluid transport. The electrokinetic fluid transport can be by capillary electrophoresis. In generally, the step of transporting the analyte may be by electrical, mechanical, centrifugal, magnetic, pneumatic, pressure-activated, or vacuum-activated fluid transport methods.

Analyzing the analyte at the thick-film electrode by electrochemical detection can include amperometric detection, including fixed potential and potential-step amperometric detection. Analyzing can also include stripping potentiometry and voltammetric detection.

In this method, the distance between the thick-film electrode in fluidic connection with the outlet end of the microfluidic channel and the microfluidic channel can be fixed, and is preferably a distance of from about 1 $\mu$m to about 500 $\mu$m, and preferably between about 50 $\mu$m and about 100 $\mu$m. The thick-film electrode can be a carbon ink electrode, and can optionally include a metal conducting coating, and in general can include metals, inorganic dopants, organic dopants, nucleic acids, catalytic surface modifiers, enzymatic surface modifiers, or permselective film coatings.

The fluid solution of the method can be a buffer solution. Any of a variety of reactants, if employed, may be used, including enzymes and derivatizing agents. The analyte can be a nitroaromatic compound, catecholamine, hydrazine compound, phenolic compound, enzyme-specific compound, amino acid, nucleic acid, metal ion or anion. In the case of nucleic acids, the analyte may be DNA, scDNA, ssDNA, dsDNA, RNA or tRNA.

A primary object of the present invention is to provide a method and apparatus to combine microfluidic separation with the ease, cost-advantages and simplicity of thick-film electrochemical detection.

Another object of the present invention is to provide a method and apparatus for separation and identification of a wide range of analytes using microfluidic separation and thick-film electrochemical detection.

Another object of the present invention is to provide a method and apparatus for an integrated, on-chip combination reaction, separation and electrochemical detection microsystem.

Another object of the present invention is to provide an apparatus wherein the thick-film electrochemical detection component may readily be detached from the microfluidic reaction and separation component and replaced.

A primary advantage of the present invention is the ease of use and cost advantage resulting from use of thick-film electrochemical detection combination with microfluidic devices, including microfluidic reaction and separation.

Another advantage of the present invention is that the thick-film electrode may be fabricated by screen printing.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 27 is a calibration plot for glucose and other analytes.

Figure 1A:
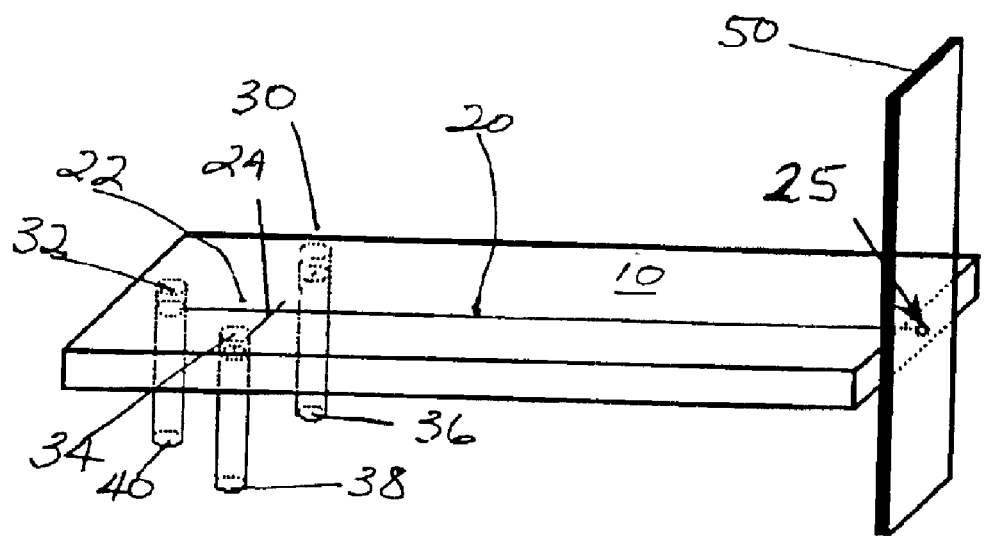
FIG. 1a to 1d schematically illustrates an embodiment of an apparatus in accordance with this invention.

DESCRIPTION OF THE PREFERRED EMBODIMENTS BEST MODES FOR CARRYING OUT THE INVENTION

This invention provides for microfluidic systems, including microfluidic separation systems, with thick-film electrochemical detection. The detector component is designed so that it may be conveniently and rapidly replaced, thereby adding versatility to the microfluidic separation and electrochemistry operation, particularly in applications requiring frequent electrode replacement.

The microfluidic separation component may be any means or method of microfluidic separation. In general, this component will consist of at least one channel or fluid conduit, and generally two or more intersecting channels or fluid conduits, and a means for pumping or movement of fluid through one or more channels or fluid conduits. In a preferred embodiment, electoosmotic flow is used to provide movement fluid through microchannels in the microfluidic separation component. One form of electoosmosis that may be employed is electrophoresis, and specifically capillary electrophoresis (CE), which includes a variety of forms of separation electrophoresis, including but not limited to capillary zone electrophoresis, capillary gel electrophoresis, capillary isoelectric focusing, capillary isotachophoresis, micellar electrokinetic chromatography and the like. By use of "CE" all of the foregoing are intended to be included. Besides CE, other modes and methods of electroosmotic, electophoretic, dielectrophoretic, electrokinetic or the like movement and separation of fluids may be employed. In general, all such modes and methods are referred to as electrokinetic modes and methods of movement of fluids.

In general, all modes and methods of electrokinetic movement of fluids, including CE, will incorporate one or more electrodes, and generally an electrode at or near to the end of each channel or fluid conduit, or in reservoirs or other areas to which such ends of such channels or fluid conduits are in fluidic communication. By application of electrical potential, fluid transfer may be initiated, movement flow rates regulated, transfer from one channel or fluid conduit to an intersecting channel or fluid conduit controlled and the like.

It is also possible and contemplated that mechanical or other pressure-driven flow devices may be used, including eternal pumps, microfabricated pumps and the like. In the case of microfabricated pumps, such components may form a part of the microfluidic separation component. The motive force employed in driving the fluids may be electrical, mechanical, centrifugal, magnetic, pneumatic, pressure-activated or any other means known in the art. The pumping may be positive, resulting in a pumping pressure, or may be negative, resulting in a vacuum draw.

In general, the channels or fluid conduits, which may function as microcapillaries, may be of any desired cross-sectional shape, and may be of any longitudinal configuration. Thus the cross-sectional shape may be rectangular, square, circular, half-circular, ellipsoidal, or any other geometric shape, regular or irregular. In a preferred embodiment, the cross-section is constant over the longitudinal dimension, or constant within limits of standard manufacturing procedures, so that the volume per given unit length of the channel or fluid conduit is constant, again within limits of standard manufacturing procedures. In general, the dimensions of the cross-sectional shape (the height, width or any diameter) will generally be at least about 1 $\mu$m, usually at least about 10 $\mu$m, and is usually no more than about 500 $\mu$m, and preferably no more than about 100 $\mu$m. The equivalent inside bore diameter is from about 1 to about 300 $\mu$m, and is typically from about 20 to 120 $\mu$m. In one embodiment, the cross-section is half-circular, with a maximum depth of about 20 $\mu$m and a width, at the top, of about 50 $\mu$m.

The longitudinal configuration may be any configuration that may be described. Thus the channel or fluid conduit may be straight, curved, spiral, serpentine or the like. The required length of the channel or fluid conduit is generally related to the separation technique, media if any, analyte and the like. The length will generally be at least about 1 mm, usually at least about 10 mm, and is usually no more than about 500 mm, and preferably no more than about 100 mm. In one embodiment, the effective length of the primary separation channel or fluid conduit is about 72 mm.

The channels or fluid conduits are generally a part of a planar substrate. Such channels or fluid conduits may be made by any means known in the art, including microphotolithographic techniques, chemical etching, laser cutting, molding, embossing, drilling, mechanical cutting, machining or scoring, grooving or the like. The planar substrate is conventionally substantially flat, or has at least one substantially flat surface into which the channels or fluid conduits are laid. However, it is also possible and contemplated that the surface of the planar substrate into which the channels or fluid conduits are laid may be curved or otherwise other than flat.

The planar substrate may be made of any material which may be employed in conjunction with the analyte, the buffer or other fluids, and the motive force employed for pumping or movement of fluid through one or more channels or fluid conduits of the microfluidic separation component. Because the method of detection is by thick-film electrochemical detection, there is no need for the planar substrate to transmit light, permit fluorescent observation or the like required by other detection modalities, such as laser fluorescence. Thus the planar substrate, or a portion thereof wherein one or more channels or fluid conduits are located, may be constructed of fused-silica, glass, other silica-based substrates, gallium-based substrates, plastics, polymeric materials, elastomeric materials, and the like. In one embodiment, a solid or semi-solid substrate that is compatible with microfabrication techniques, such as photolithography, is employed.

It is also possible and contemplated that the inside surface of one or channels or fluid conduits is coated with a material, which material may be used to provide strength, assist in regulating the motive force employed for pumping or movement of fluid, provide compatibility with buffers or analytes, or the like. Such material may be any art conventional material, including polymeric materials, and may thus include silicon-based coatings, polyacrylamides, polyvinyls, polyethylenes, polyesters, polyethers, Teflon™ (DuPont), Nafion™ (DuPont), and the like. The material may be applied by any known coating method, including plasma deposition, sputtering, electrochemical attraction, plating, immersion, spraying, or the like.

The interior surface of the channel or fluid conduit may be altered, such as by application of a coating or mask, such that portions thereof are relatively hydrophobic and other portions thereof are relatively hydrophilic.

At each end of each channel or fluid conduit there is located at least one of an inlet port, channel outlet, reservoir, cavity, chamber, well or the like. Such components may be in series, so that, for example, an inlet port is in fluid connection with a reservoir or other cavity, which in turn is in fluid connection with one end of the channel or fluid conduit. The reservoir, cavity or similar structure may serve any of a number of purposes, including as an incubation chamber, reagent reservoir, running buffer reservoir, sample reservoir, separation chamber, reaction chamber, detection chamber in fluid communication with the thick-film electrochemical detection component, injection waste reservoir, enrichment chamber or the like. Reservoirs, cavities and the like may be of any size and volume consonant with the intended purpose, and may include cavities or wells, enlarged portions of the channel, or the like. In one embodiment, the channel outlet is in connection with a cavity, such as a detection chamber in fluid communication with the thick-film electrochemical detection component. In another embodiment, an inlet port is in fluid communication with a cavity, such as an incubation chamber, reagent reservoir, running buffer reservoir, sample reservoir, or reaction chamber, which in turn is in fluid communication with the channel or fluid conduit. It is also possible and contemplated that two or more channels or fluid conduits may be in fluid communication with one cavity, such as an incubation chamber, reagent reservoir, running buffer reservoir, sample reservoir, separation chamber or reaction chamber, and further is contemplated that the motive force employed for pumping or movement of fluid may selectively cause movement of fluid through one or more of the channels or fluid conduits. In one embodiment, a selective electrokinetic system is employed, whereby movement of fluid may be effected to one or more selected channels or fluid conduits in fluid communication with a cavity, including an intersecting channel or fluid conduit, such as by selective application of potential to selected electrodes located at or near ends of or along the length of some or all of the channels or fluid conduits.

Through use of appropriate cavities, chambers or reservoirs, any of a wide variety of either pre-separation or post-separation derivatization reactions may be conducted. Such cavities, chambers or reservoirs may optionally be heated, such as by heating resistors, to optimize the derivatization method employed. Through use of such derivatization methods, electrochemical detection may be employed with selected non-electroactive analytes.

Such channels or fluid conduits may intersect other channels or fluid conduits, which intersection may be at any angle. It is possible and contemplated that more than two such channels or fluid conduits may intersect at a given point. It is also possible and contemplated that a multiplicity of channels or fluid conduits, such as three or more, meet at a given point, and are thereby in fluid connection one with the other, without any given channel or fluid conduit continuing past such point, as in a star-burst configuration. The intersection may optionally, but need not, form a cavity, well or reservoir. By selective application of the motive force employed for pumping or movement of fluid, fluids may enter through any one or more of the intersecting channels or fluid conduits, and may be caused to exit or outlet through any other one or more of the intersecting channels or fluid conduits. In this way, the intersection acts as a valve, which may be a selectable and changeable valve, such that the operator may select one or more inlet channels or fluid conduits, and one or more outlet channels or fluid conduits. In one embodiment, a selective electrokinetic system is employed, whereby movement of fluid may be effected to one or more selected inlet channels or fluid conduits in fluid communication with one or more selected intersecting outlet channels or fluid conduits, such as by selective application of potential to selected electrodes located at or near ends of or along the length of some or all of the channels or fluid conduits.

The planar substrate may form a part of an integrated on-chip combination reaction, separation and detection microsystem. The integrated on-chip microsystem, including the planar substrate, may further include electrodes, printed circuit connectors and the like, particularly for the application of electrokinetic flow, CE and the like. Such electrodes may conventionally be platinum wires, but may be any convenient type capable of applying an appropriate electric field to the fluid or other medium in the channel or fluid conduit with which they are associated. Such electrodes may thus be made of any suitable conductive material, and may be applied by any means known in the art, including sputtering, plating, painting, and the like, as well as use of wires, strips, rods or the like as electrodes. In general, at least one electrokinetic flow electrode is placed at or near each end of any given channel or fluid conduit, though it is possible that a single electrode, such as an electrode placed at an intersection of two or more channels or fluid conduits, or in a reservoir or cavity with which two or more channels or fluid conduits are in fluid communication, may serve as a terminus electrode for more than one channel or fluid conduit. It is also possible and contemplated that a multiplicity of electrodes, such as more than two, are placed along the length of the channel or fluid conduit, such that, for example, the rate of flow of fluid through the channel or fluid conduit may be altered along the length of such channel or fluid conduit. Connections to such electrodes may form a part of the integrated on-chip microsystem, and may terminate in one or more plugs, connector strips, pins, pin sets, chip holders and connectors, or the like.

Such electrokinetic electrodes are connected to a high-voltage power supply, and preferably a power supply with multiple independent and selectable voltage terminals for connection to each electrode. Any effective driving voltage may be employed; in general, the driving voltage for both movement of fluid and switching between modes, reservoirs, channels or the like is between about 0 and about +30,000 volts (V) and preferably between about 0 and about +4000 V. The power supply may be integrated into a computer-based system, and may further be integrated into a computer-based system which also controls amperometric detection using the thick-film electrochemical detection component, which system may be programmable, include appropriate feed-back and control systems, record data, produce output records of data, and the like.

The integrated on-chip combination reaction, separation and detection microsystem may include a multiplicity of CE separation channels or fluid conduits, which may permit simultaneous detection of different analytes in a common sample, detection of the same analyte in multiple different samples, or any combination thereof. In the case of detection of different analytes in a common sample, it is contemplated that a sample inlet port may be connected to one or more sample reservoirs, with any number of separation channels or fluid conduits in fluid connection with such reservoir or reservoirs. In one embodiment, the separation channels or fluid conduits are arranged in a star-burst configuration, with a multiplicity of separation channels or fluid conduits emanating from and in fluid connection with a common central sample reservoir, which in turn is in fluid connection with an inlet port. It is also possible and contemplated that the multiplicity of separation channels or fluid conduits are in fluid communication with one or more reagent reservoirs, running buffer reservoirs and the like, such that different reagents, buffers or the like may be selected for different separation channels or fluid conduits.

The separation channels or fluid conduits may include therein a separation matrix element, such as a gel, membrane, polymeric material, polymeric particles or the like, including those materials and elements used in conventional separation techniques, such as chromatography, electrophoresis, and other analytical separation methods and techniques. Use of such sieving or separation methods may reduce the length of the separation channel or fluid conduit required to obtain the desired degree of separation.

Any of a wide variety of buffers, including conventional buffers, may be employed in the integrated on-chip combination reaction, separation and detection microsystem of this invention. The selection of buffers is largely dependent on the analyte, the specific separation technique employed and the specific detection system employed. Thus, MES, borate, SDS, PBS, borate/phosphate, phosphate, and the like may be employed, as well as buffers such as HEPES, MOPS, MES, Tricine, Tris, acetate, citrate and the like. The buffers may include additives such as alcohols, surfactants, detergents and the like. Exemplary buffer systems include: a) 25 mM 2-(4-morpholino)ethanesulfonic acid hydrate at pH 6.5; b) 15 mM sodium borate with 25 mM sodium dodecyl sulfate at pH 8.7; c) 10 mM phosphate at pH 7.3 with 1 mM potassium chloride; d) mixed 10 mM each borate and phosphate buffer at pH 8.0; e) 10 mM borate buffer at pH 10.5; f) 10 mM phosphate buffer at pH 7.4; and g) 20 mM sodium borate with 30 mM sodium dodecyl sulfate at pH 9.4. Such buffers may optionally be filtered, such as by use of a 0.45 $\mu$m filter, prior to use.

Any of a wide variety of reactants may be employed, either as components of the buffer, or as separate reactants introduced into the system through an inlet port, and optionally placed into a reaction chamber. Typical reactants include any of a wide variety of enzymes, such as glucose oxidase enzyme. There are over 200 dehydrogenase redox enzymes and over 100 oxidase enzymes known to the art which generate electrochemically detectable products. It is also possible and contemplated that multiple simultaneous oxidase- and dehydogenase-based reactions may be conducted. Where a reactant is employed, there may be multiple cavities, wells, chambers or reservoirs, such as a buffer reservoir, which contains only buffer, a reactant reservoir, which contains a mixture of a reactant with a buffer, and the like. Where pre-separation or post-separation derivatization reactions are conducted, such reactants also include those required for the derivatization reaction. Thus, such reactants may include o-phthalaldehyde, 2-mercaptoethanol, and the like, together with other components such as sodium borate, methyl alcohol and the like. In the event that a derivatization reaction is performed, then a derivatization reaction chamber may be provided.

The separation channels or fluid conduits are in fluid connection with the thick-film electrochemical detector component forming a part of the integrated on-chip combination reaction, separation and detection microsystem. In one embodiment, a channel outlet from the separation channel or fluid conduit is in fluid connection with the surface of a thick-film working electrode, such as a screen-printed carbon-based working electrode. The distance between the channel outlet and the electrode surface may be modified as required for the analyte, separation technique and electrochemical detection technique, but in general such distance will be between about 1 $\mu$m and about 500 $\mu$m, and preferably between about 50 $\mu$m and 100 $\mu$m. The distance may be controlled by a thin-layer spacer of suitable thickness.

The thick-film electrochemical detector component may be detachable from the reaction and separation components of the integrated on-chip combination reaction, separation and detection microsystem. Thus the thick-film electrochemical detector component may be affixed to the remaining components of the microsystem by a snap, friction fitting, set screw, slide fastener, dip, or the like, and may be constructed such that the thick-film electrochemical detector component may be rapidly replaced by the user, such as in less than one minute, and preferably in less than about ten seconds. Such replacement may be performed to replace a fouled, passivated or damaged thick-film electrochemical detector component, to substitute a thick-film electrochemical detector with different working electrode components, and the like.

In one embodiment, the thick-film electrochemical detector component is perpendicular to the separation channel or fluid conduit. Thus the channel outlet terminates opposite of, and within the specified distance from, the surface of the working electrode forming a part of the thick-film electrochemical detector component. In another embodiment, the planar substrate containing the separation channel or fluid conduit is parallel to and in communication with the thick-film electrochemical detector component. For example, the thick-film electrochemical detector component may form a lower plate, with the planar substrate containing the separation channel or fluid conduit forming an upper plate, such that the outlet channel is within a specified distance from the surface of the working electrode. In this embodiment, the planar substrate may be plastic or another polymeric material, and have photolithographed, cut, etched or otherwise placed thereon the channels, fluid conduits, cavities and the like, with the lower plate forming a seal or bottom surface for such channels, fluid conduits, cavities and the like.

The thick-film electrochemical detector may be made on a ceramic wafer, or optionally on any other material that is suitably inert and non-conductive, such as preferably a plastic substrate. The detection reservoir, which is in fluid connection with the outlet channel, may include therein one or more electrodes, such as one or more platinum wires and an Ag/AgCl wire. One or more of the platinum wires may serve as a contact for the high-voltage power supply, serving as an electrokinetic flow electrode. An additional platinum wire and the Ag/AgCl wire may serve as counter and reference electrodes, respectively, for detection. Detection may be by amperometric, voltammetric or potential detection. The Ag/AgCl wire may be prepared by electrochemical oxidization of a silver wire in 0.10 M hydrochloric add. In alternative embodiments, other electrodes, known in the art, may serve as the counter and reference electrodes. It is also possible that a two electrode system is used, such as for amperometric detection, consisting of the screen-printed or otherwise fabricated thick-film working electrode and a reference electrode.

In one embodiment, a 100×100×0.64 mm alumina ceramic plate is used for the thick-film electrochemical detector. The screen-printed working electrode is printed with a printer, such as a semi-automatic printer (Model TF 100, MPM, Franklin, Mass.), with printing through patterned stencils (100 $\mu$m thick, Specialty Photo-Etch, Inc., TX) onto the alumina ceramic plate. Each plate consists of 30 strips (33.3×10.0×0.64 mm) with each strip being defined by a laser pre/semi cut. A carbon ink working-electrode layer (Acheson ink Electrodag 440B, Acheson Colloids, Ontaria, Calif.) of 0.3×8.0 mm is first printed on each of the strips of the alumina ceramic plate and is cured at about 100° C. for about 30 minutes. A silver ink (Ercon R-421(DRE-68)) contact layer of 1.5×21.0 mm, partially overlapping the carbon layer, is printed and cured at about 100° C. for about 30 minutes. An insulating ink (Ercon R-488CI-G1Insulator Green) layer is subsequently printed to cover the carbon-silver junction and to define the working electrode area, 0.30×2.5 mm, on one end, and to expose the contact area on the other side. The strips are then cured at about 100° C. for about 120 minutes. The cured layers of carbon, silver, and insulator have a thickness of approximately 10, 28 and 70 $\mu$m, respectively.

The carbon ink working electrode active area may be subsequently modified. In one embodiment, a palladium-modified screen-printed electrode is prepared by scanning or cycling the potential between about +0.6 V and −0.6 V, against the Ag/AgCl reference electrode, for 60 cycles in a 0.5 M HCl solution containing 1000 ppm Pd(VI). In another embodiment, the carbon working electrode area is coated with gold by applying a pulse waveform, again against the Ag/AgCl reference electrode, in a solution containing 300 ppm Au(III), 0.1 M NaCl and 1.5% (w/v) HCl. The surface of the working electrode may similarly be modified by other means known in the art, including coating with other metals, use of various dopants, use of catalytic or enzymatic surface modifiers, permselective film coatings, or the like.

The working electrodes via the silver ink contact layers, and the platinum wires and the Ag/AgCl wires serving as counter and reference electrodes, are connected, through one or more plugs, connector strips, pins, pin sets, connectors, or the like, to a detection device, such as an amperometric detection device. In one embodiment, a device such as an Electrochemcial Analyzer 621 (CH Instruments), connected to a computer, is employed. In general, the amperometric detection device should have such inputs as are required for the number of working electrodes to be detected, and should work over a suitable scanning voltage range, from a potential of between about +1.0 and −1.0 V against the reference electrode, and cycling in a variety of wave forms over a range of pulse widths. The amperometric detection device may be integrated into a computer-based system, and may further be integrated into a computer-based system which also controls the high-voltage power supply, which system may be programmable, include appropriate feed-back and control systems, record data, produce output records of data, and the like. It is possible and contemplated that the entire integrated on-chip combination reaction, separation and detection microsystem, including the microfluidic separation component, the thick-film electrochemical detection component, the high-voltage power supply, the amperometric detection device, data recording elements and other components parts may be made into a single device, with a removable and replaceable thick-film electrochemical detector component, and optionally a removable and replaceable microfluidic separation component. Such single device may be a portable device, and may further be a hand-held device. Such device may be connected to data acquisition devices by any means known in the art, including wires, infrared, radio or the like.

Amperometric detection may be by either fixed-potential and potential-step amperometric detection. However, it is also possible and contemplated that other electrochemical detection modes may be employed, depending on the specific analyte, microfluidic or separation system, reactants if any, detector components and the like, as are taught generally in J. Wang, *Analytical Electrochemistry*, $2^{nd}$ Ed., Wiley-VHC, New York, 2000. Thus a variety of modes of electrochemical detection may be employed, including potential-sweep or scanning potential voltammetric modes, cyclic voltammetry, pulse voltammetry, including normal-pulse, differential-pulse, square-wave and staircase voltammetry, potentiometric stripping analysis, adsorptive stripping voltammetry and potentiometry, and the like.

In operation, the channels may be rinsed with a suitable cleaning solution, such as sodium hydroxide, hydrochloric add, deionized water or the like. Electrokinetic transport may be used for cleaning the channels. To perform separations, the appropriate reservoirs are filled, or partially filed, with the appropriate buffer, analyte or reactants. In one embodiment, from about 10 $\mu$L to about 250 $\mu$L of buffer is placed in the buffer reservoir, and from about 10 $\mu$L to about 250 $\mu$L of sample containing the analyte is place in the sample reservoir. In another embodiment, about 80 $\mu$L of reactant is placed in a reactant or reagent reservoir, two or more buffer reservoirs have about 80 $\mu$L of buffer placed in each, and about 80 $\mu$L of sample, containing the analyte or analytes, is placed in a sample reservoir. Such placement may be by any art conventional means, including use of pipettes, micropipettes, pipette tips and the like.

Through selective application of high voltage to selected electrokinetic flow electrodes located at or near ends of or along the length of some or all of the channels or fluid conduits, in cavities or reservoirs, or the like, movement of fluid may be controlled. For example, in a system with an injection channel, separation channel and sample reservoir, the injection channel may be filled with sample solution by application of about +1500 V for about 30 seconds to the sample reservoir with the detection reservoir grounded and the buffer reservoir floating, it being understood that the applied voltage and time may be modified as required for the specific device and conditions. Where both a reactant or reagent reservoir and a sample reservoir are employed, a voltage of about +1500 V for about 60 seconds may be applied to both, with the detection reservoir grounded and other reservoirs floating, such that the reaction chamber is filled at a constant mixing ratio. Different sample and reactant mixing ratios may be applied by independently altering the current flows to the reactant and sample reservoirs, such as through use of different resistors.

For performing assays, a "sample plug" may be loaded into the separation channel, such as by application of +1500 V to the sample reservoir, injection channel, reaction chamber, combination of the sample and reaction reservoirs or the like, for a suitable time, such as about three seconds. An injection time of three seconds, in certain systems, corresponds to an injected volume of about 2 nL. The injection time and voltage may be altered as required to produce the desired injection volume. Separation is performed by applying an appropriate voltage, such as from about +1000 to about +3000, to the running-buffer reservoir with the detection reservoir ground and other reservoirs floating. Voltage is applied for so long as is required to obtain desired electrochemical data.

Electrochemical detection is by amperometric detection over a suitable voltage range, from a potential of between about +1.0 and −1.0 V against the reference electrode, with an appropriate time resolution, such as about 0.1 seconds.

Figure 1B:
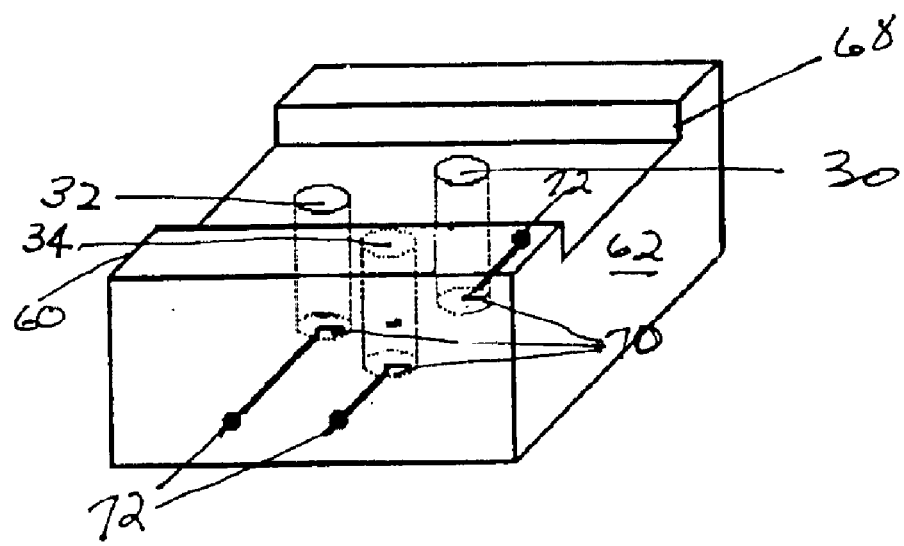

Turning now to the figures, in FIG. 1a an apparatus of this invention is depicted, with microfluidic separation component 10, and detection component 50. Separation component 10 may be a glass microchip, as described above, or any other suitable material, on which is made a separation channel 20, which may be made by microphotolithographic techniques. Intersecting channel 20 is injection channel 24; the separation channel 20 continues along portion 22 from the intersection with injection channel 24. Separation channel 20 terminates in channel outlet 25. Reservoir 30 is a sample reservoir, accessed by pipette injection port 36; Reservoir 32 is an additional reservoir, which in some embodiments is not employed and in others is used as the reactant reservoir; reservoir 32 is accessed by pipette injection port 46, which in embodiments in which reservoir 32 is not employed is blocked. Reservoir 34 is a buffer reservoir or running buffer reservoir, accessed by pipette injection port 38. As shown in FIG. 1b, the reservoirs 30, 32 and 34 actually form a part of base 62, which may be made of Plexiglass or any other plastic or formable or machinable material; base 12 is sealed to separation microchip 10, such as by silicone grease or any other form of sealant. A recessed groove 68 is provided to secure separation microchip 10 such that the reservoirs 30, 32 and 34 are in proper alignment with channels 22 and 24. Electrodes 70 are in the base of each of reservoirs 30, 32 and 34, and may be a platinum wire, serving as a contacting for the high-voltage power supply. Each of electrodes 70 are connected to connector 72, to which electrical contact is made.

Figure 1C:
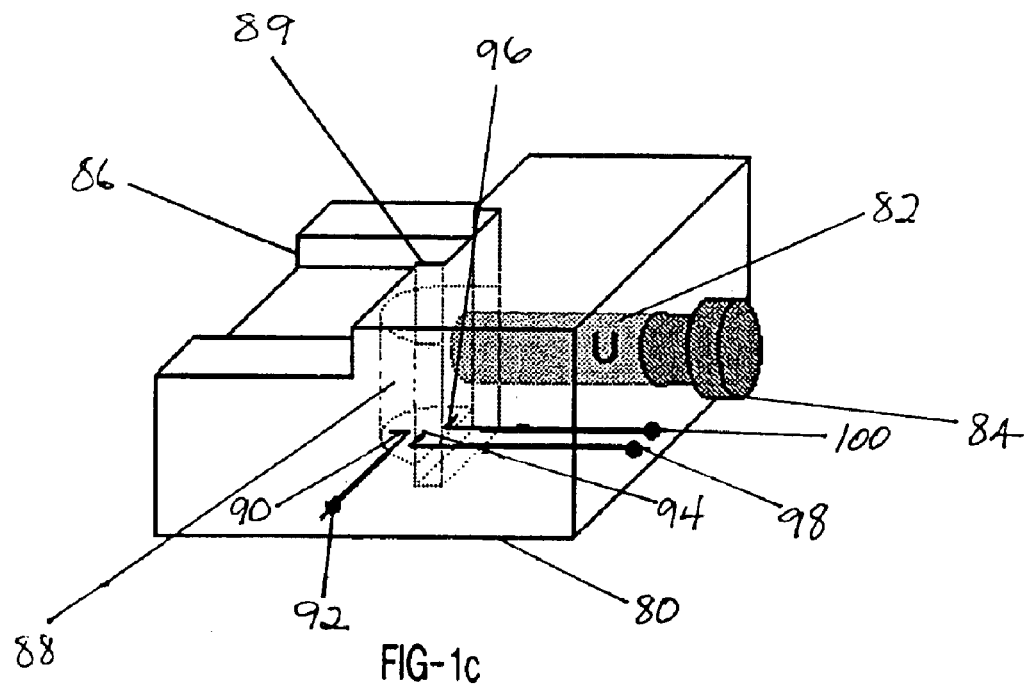

In FIG. 1c is provided a detection component holder 80, which holder 80 may form a part of base 62, or may be separate as depicted. Holder 80 is similarly fabricated from Plexiglass or any other plastic or formable or machinable material. Holder 80 includes detection reservoir 88 with slot 89 for receiving detection component 50. A recessed groove 86 is provided to secure separation microchip 10. At the base of detection reservoir 88 is a high-voltage power electrode 90, such as a platinum wire, connected to connector 92. Also at the base of detection reservoir 88 is counter electrode 94, connected to connector 98, and reference electrode 96, connected to connector 100. Counter electrode 94 may be a platinum wire, or any other suitable counter electrode material for use in amperometric detection. Reference electrode 96 may be an Ag/AgCl wire, such as prepared by electrochemical oxidation of a silver wire in 0.10 M hydrochloric acid or any other suitable reference electrode material for use in amperometric detection. Also forming a part of holder 80 is threaded cylinder 82 with which plastic screw 84 is threadably engaged, and tightly secures detection component 50 in slot 89.

Figure 1D:
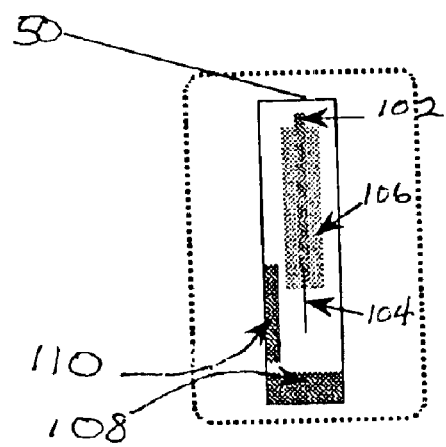

In FIG. 1d is provided detection component 50, on which is screen printed working electrode 104, which may be a carbon ink based strip, approximately 0.3×8.0 mm, and 10 µm thick. A silver ink contact layer 102 is printed over a portion of the working electrode 104, the silver ink contact layer 102 being approximately 1.5×21.0 mm, and approximately 28 µm thick. An insulating Link layer 106 is printed over the working electrode 104 and silver ink contact layer 102, forming and defining a working electrode area of approximately 0.3×2.5 mm and leaving the end of silver ink contact layer 102 available for connecting to an amperometric detection device. The insulator has a thickness of 70 µm. Also provided are spacers 108 and 110 which control the distance between the working electrode 104 and the channel outlet 24; such spacers 108 and 110 have a nominal thickness of 60 µm and may be made of tape or another suitable material.

Figure 2:
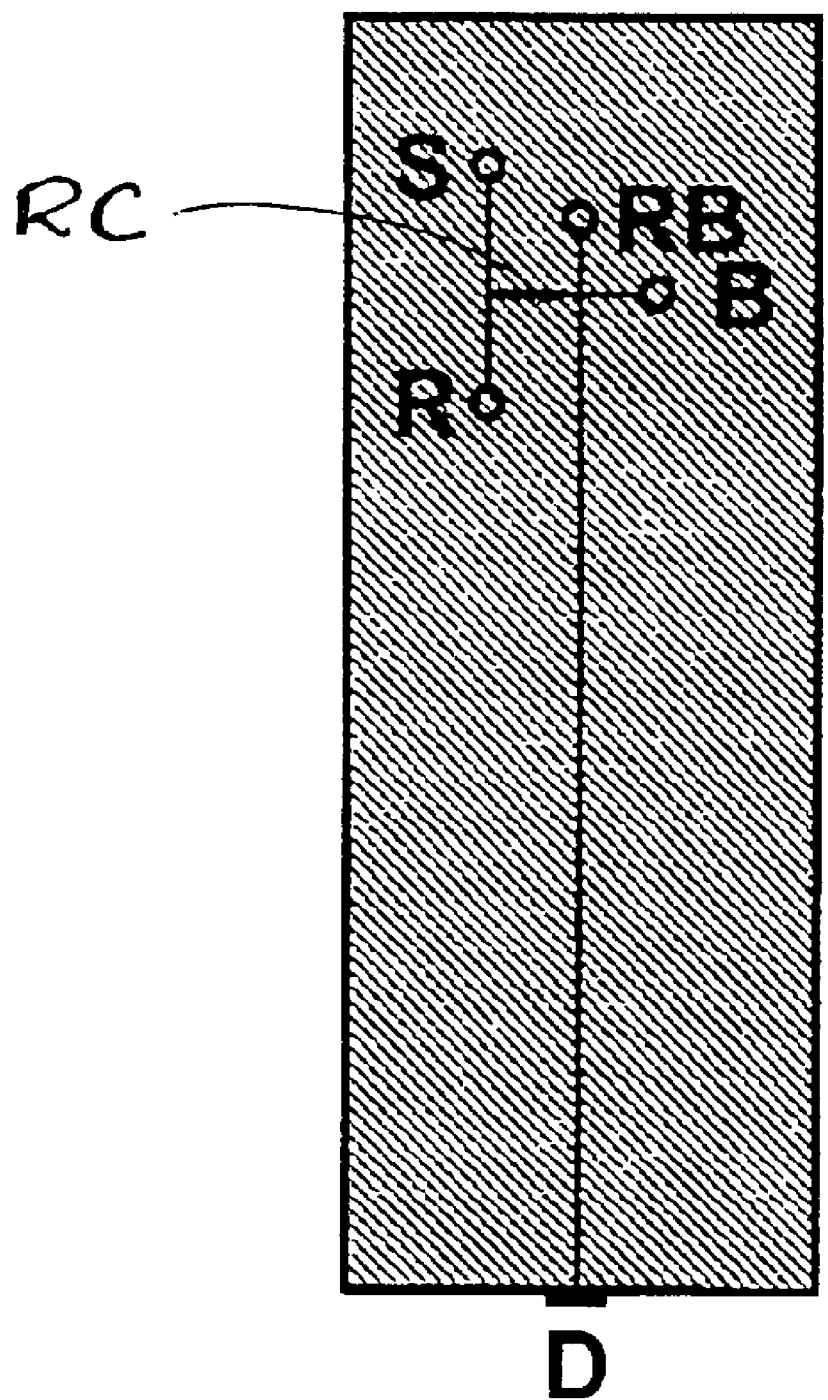
FIG. 2 schematically depicts an alternative configuration of the separation and reaction component for use with derivatized reactions in accordance with this invention.

FIG. 2 is a schematic of an integrated reactor and separation microchip with electrochemical thick-film detection. In FIG. 2, S is the sample reservoir, R is the reagent reservoir, RB is the running buffer reservoir, B is the buffer reservoir, RC is the reaction channel and D is the detector, a thick-film working electrode. Electrodes for electrokinetic movement of fluids, or other fluid transfer components, are not shown. The reaction chamber, 200 µm wide and 3.6 mm long, is connected through 50 µm wide channels to the reagent and sample reservoirs at one side, and to a four-way injection cross at the other side. The separation channel is 74 mm long and 50 µm wide.

Figure 3:
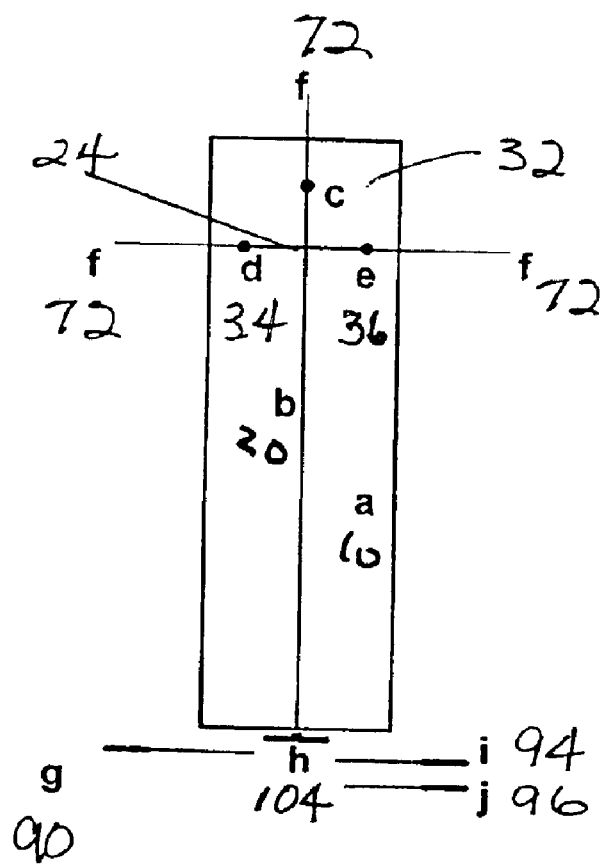
FIG. 3 schematically depicts an alternative configuration of the separation component in accordance with this invention.
Figure 4:
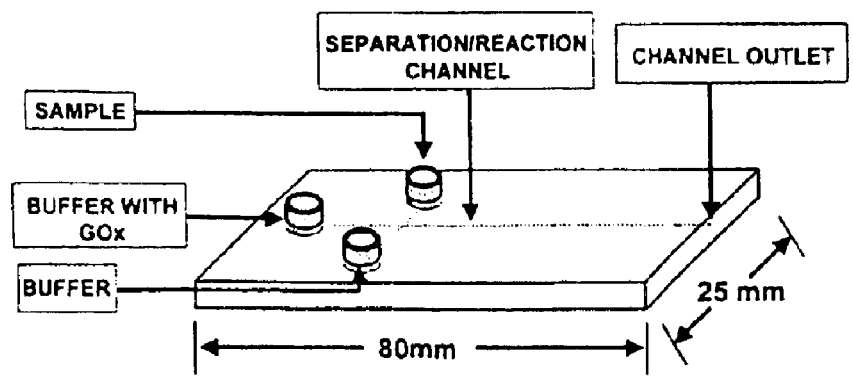
FIG. 4 depicts an alternative configuration of the separation and reaction component for use in bioassays in accordance with this invention.

FIG. 3 is a schematic of the device of FIG. 1. FIG. 4 is the separation and reaction component of a device used for enzymatic reactions and separations, with a reservoir containing glucose oxidase (GOx) in combination with buffer, and a separate reservoir containing buffer. In use, the sample and buffer with GOx are both simultaneously loaded into the separation/reaction channel, and then run using the buffer, such that the enzymatic reaction and separation both occur in the separation/reaction channel.

Figure 34:
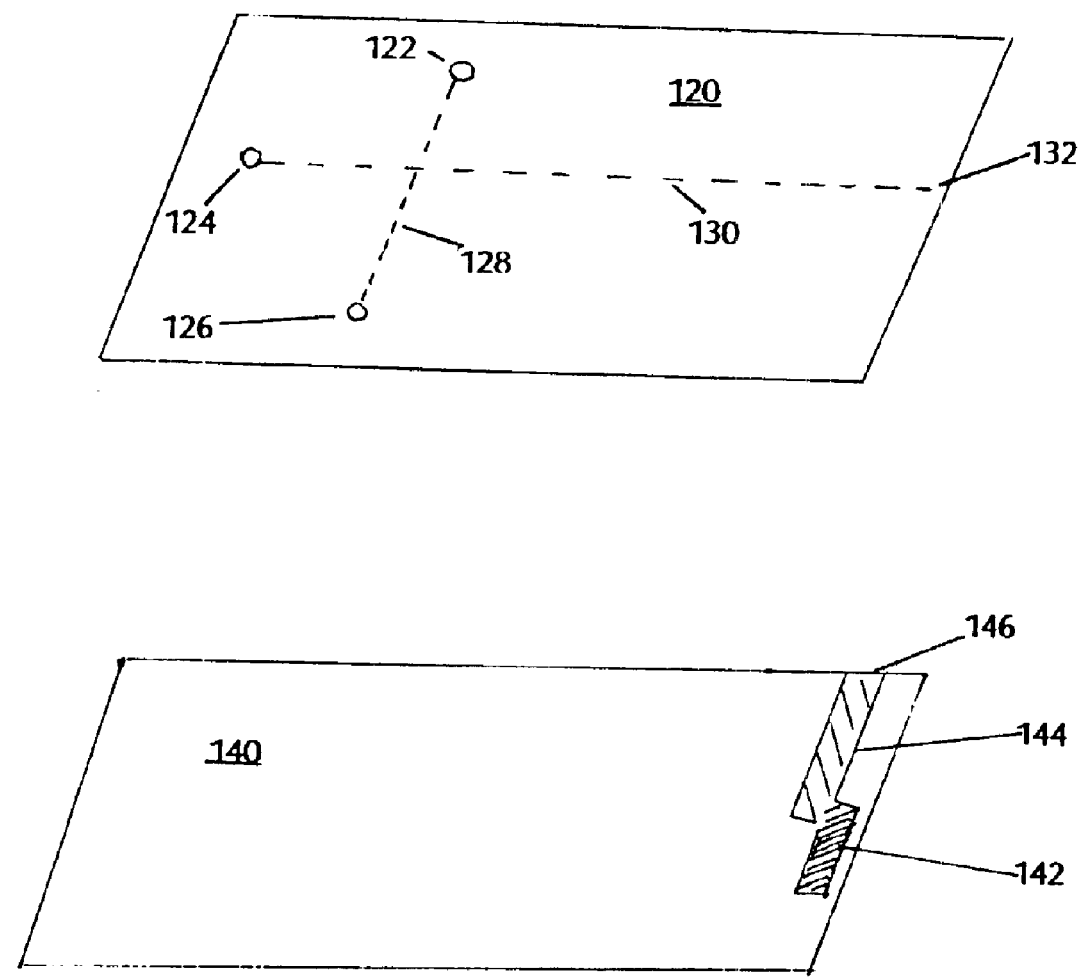
FIG. 34 schematically depicts a microsystem in accordance with this invention with parallel separation and detection components; and, FIG. 35 schematically depicts a multi-channel microsystem in accordance with this invention.

FIG. 34 is an embodiment in which the separation component 120 is parallel to the detection component 140. Separation component 120 includes reservoirs 122, 124 and 126, which may be sample, buffer or reactant reservoirs, with reservoirs 122 and 126 connected by channel 128. The channel 130 is a separation channel, terminating in outlet 132. Separation component 120 is in contact with, and optionally detachable from, detection component 140, such that the outlet 142 is between about 1 µm and 500 µm, and preferably between about 50 µm and 100 µm, from the thick-film working electrode 132. An insulating layer 144 covers that portion of the screen-printed working electrode not in fluid contact with outlet 142, with a connector 146 for electrical contact. This embodiment may also include a waste or detector reservoir, electrokinetic electrodes, reference electrodes and other features shown on FIG. 1.

Figure 35:
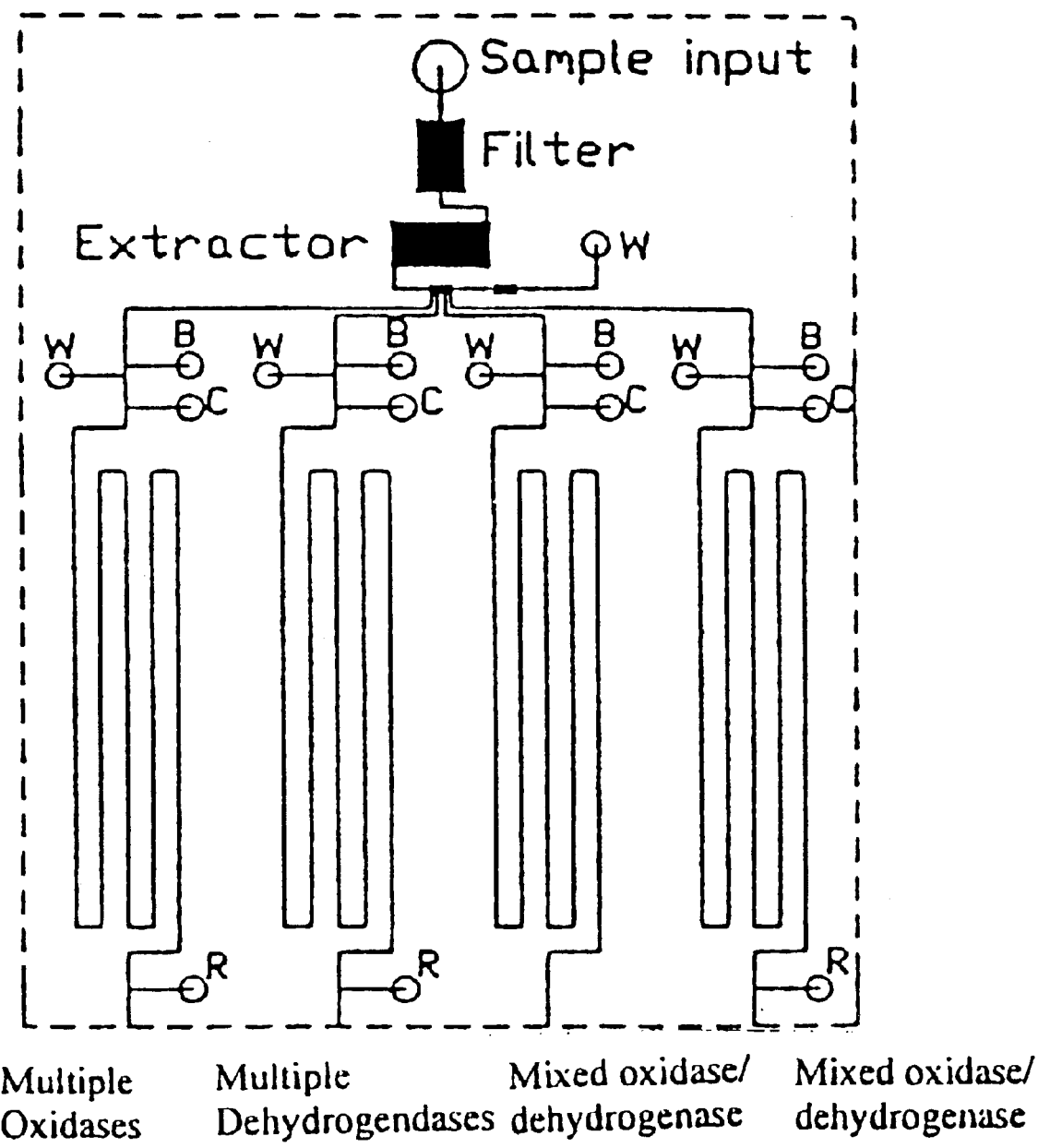

FIG. 35 depicts a multi-channel microchip for parallel emzyme-based assays using a single sample. This format also provides for both pre- and post-separation derivatization reactions.

The device and methods of this invention may be employed for the detection of any of a wide range of substances. These include nitroaromatic compounds, catecholamines, hydrazine compounds, phenolic compounds, glucose, lactate, amino acids, nucleic acids, including DNA and RNA, metal ions, anions, and a wide range of other compounds. In general, any electroactive analyte or derivitizable non-electroactive analyte may be detected using the device and methods of this invention.

The device and methods of this invention have particular application for detection and determination of nucleic acids. Electrophoresis is widely used for analysis of nucleic acids and similar separations methodologies may be included, including use of capillary gel electrophoresis and capillary zone electrophoresis. The methods may be employed for oligunucleutide quality control, quantitative viral load determination, gene expression studies, analysis of DNA-protein interactions, genotyping, DNA sequencing and the like.

In addition to the fixed-potential and potential-step amperometric detection modes disclosed herein, it is also possible and contemplated that potentiometric stripping measurements may be made of extremely low levels of DNA or RNA following adsorptive accumulation onto the working electrode surface. Another method of detections involves hybridization recognition at a probe-coated working electrode for sequence-selective biosensing. Both methods are described in more detail in U.S. Pat. No. 6,063,259. Scanning potential voltammetric modes are also possible and contemplated for such detection.

The device and methods of this invention may be used for any of a wide variety of medical, clinical, research, environmental, industrial or other applications. For example, devices of this invention could be used: a) to determine glucose or other analyte levels in patients; b) to monitor for presence of explosives in airports and other high security areas; c) to monitor for pollutants and contaminants in water, soil or other substrates; d) for in-process quality control in manufacturing or synthesis processes; e) for automated DNA sequencing: f) for research applications; and the like. In general, the device and methods of the invention may be used in any application wherein an analyte must be detected or quantitated.

The invention is further illustrated by the following non-limiting examples.

EXAMPLE 1

Apparatus Construction

A high-voltage power supply with an adjustable voltage range between 0 and +4000 V was employed. Glass microchannel separation chips were fabricated at Alberta Microelectronic Corp. (AMC Model MC-BF4-001, Edmonton, Canada), using standard microphotolithographic technology, including wet chemical etching and thermal bonding techniques, as depicted in FIG. 1a. The resulting glass chip 10 consisted of a glass plate (120×87 mm), with a 77 mm long separation channel 20 located between a deliberately blocked and unused reservoir 32 and the channel outlet 24 at the detection reservoir 88, and a 10 mm long injection channel 24, located between the sample reservoir and the buffer reservoir. The two channels crossed each other halfway between the sample and the buffer reservoir and 5 mm from the blocked reservoir yielding a separation channel with an effective length of 72 mm. Each channel had a half-circle cross section, with a maximum depth of 20 µm and a width of 50 µm at the top. It was constructed such that pipette tips could be inserted into holes in the buffer and sample reservoirs.

The glass chip was fixed in a laboratory-built Plexiglass holder, as depicted in FIG. 1b, with silicone grease providing sealing. The holder contained reservoirs for the sample and buffer solutions, a detection reservoir and an unused reservoir. A platinum wire was inserted into each reservoir and served as contacts for the high voltage power supply. An additional platinum wire and an Ag/AgCl wire were inserted into the detection reservoir, serving as the counter and reference electrodes, respectively, for amperometric detection. The Ag/AgCl wire was prepared by electrochemical oxidization of a silver wire in 0.10M hydrochloric acid. The detection reservoir FIG. 1c, had a special groove into which the screen-printed electrode strip FIG. 1d, fit exactly, to allow reproducible and stable positioning, perpendicular to the flow direction. The screen-printed electrode strip was further held in place by a plastic screw pressing the strip against the channel outlet. Amperometric detection was performed with an Electrochemical Analyzer 621 (CH Instruments) connected to a Pentium 166 MHz computer with 32 MB RAM.

EXAMPLE 2

Screen-Printed Electrodes

Screen-printed electrodes were printed with a semi-automatic printer (Model TF 100, MPM, Franklin, Mass.). One of three different carbon inks were utilized for fabricating the working electrode, Acheson ink Electrodag 440B (49AB90) (Acheson Colloids, Ontario, CA), Ercon Ink G-448(I) (Ercon, Waltham, Mass.) and a ESL ink RS12113 modified to contain 30% extra carbon (Electro-Science Laboratories Inc., PA). Printing was performed through patterned stencils (100 $\mu$m thick, Specialty Photo-Etch, Inc., Texas) onto 100×100×0.64 mm alumina ceramic plates. Each plate consisted of 30 strips (33.3×10.0×0.64 mm) with each strip being defined by a laser pre/semi cut. The total printing procedure consisted of the following steps. A carbon ink working-electrode layer (0.3×8.0 mm) was first printed on each of the strips of the ceramic plate and was cured at 100° C. for 30 minutes. Then, a silver Ink (Ercon R-421 (DRE-68)) contact layer (1.5×21.0 mm), partially overlapping the carbon layer, was printed and cured at 100° C. for 30 minutes. An insulating ink (Ercon R-488CI-G1 Insulator Green) layer was subsequently printed to cover the carbon-silver junction and to define the working electrode area (0.30×2.5 mm) on one end, and to expose the contact area on the other side. The strips were then cured at 100° C. for 120 minutes. The cured layers of carbon, silver, and insulator had a thickness of 10, 28 and 70 $\mu$m, respectively. Prior to use, pieces of tape (Scotch, Magic Tape 810) with a thickness of 60 $\mu$m each, were placed as shown in FIG. 1d. The tape served as a spacer, controlling the distance between the strip and the channel outlet.

EXAMPLE 3

Electrophoresis Procedure for Catecholamines and Nitroaromatic Explosives

Prior to use, the channels of the CE chip of Example 1 were treated by rinsing with a 1.0 M sodium hydroxide solution for 20 minutes, followed by deionized water for 1 minute, 1.0% hydrochloric acid for 20 minutes, and finally with deionized water for 1 minute. For the separation, the buffer and sample reservoirs in the chip holder and the corresponding pipette tips on the micro-channel chip were filled with 250 $\mu$l buffer and sample solutions, respectively. The chip was then placed in its holder with the pipette tips pointing downwards into the reservoirs and the detection reservoir was filled with buffer solution. Finally, the high voltage power supply was connected to the reservoirs. In order to fill the injection channel between the separation channel and the sample reservoir with sample solution, +1500 V was applied for 30 seconds to the sample reservoir with the detection reservoir grounded and the buffer reservoir floating. Separations were typically carried out by applying +1500 V to the buffer reservoir with the detection reservoir grounded and the sample reservoir floating.

The electrophoresis buffer consisted of MES buffer (25 mM, pH 6.5) for the separation of catecholamines, with injection or sample "loading" performed by applying +1000 V to the sample reservoir for 2 seconds with the detection reservoir grounded and the buffer reservoir floating. A buffer solution containing 15 mM borate (pH 8.7) and 25 mM SDS, was used for the separation of explosives. The injection was carried out by applying +1500 V to the sample reservoir for 3 seconds, with the detection reservoir grounded and the buffer reservoir floating. Prior to use, all buffer solutions were filtered through a 0.45 $\mu$m filter (Gelman Acrodisc) and sonicated for 20 minutes. Electropherograms were recorded after background stabilization, with a time resolution of 0.1 second, using applied detection potentials (vs. Ag/AgCl) of +0.70 V for catecholamines and −0.70 V for explosives.

EXAMPLE 4

Characterization and Optimization

Figure 5:
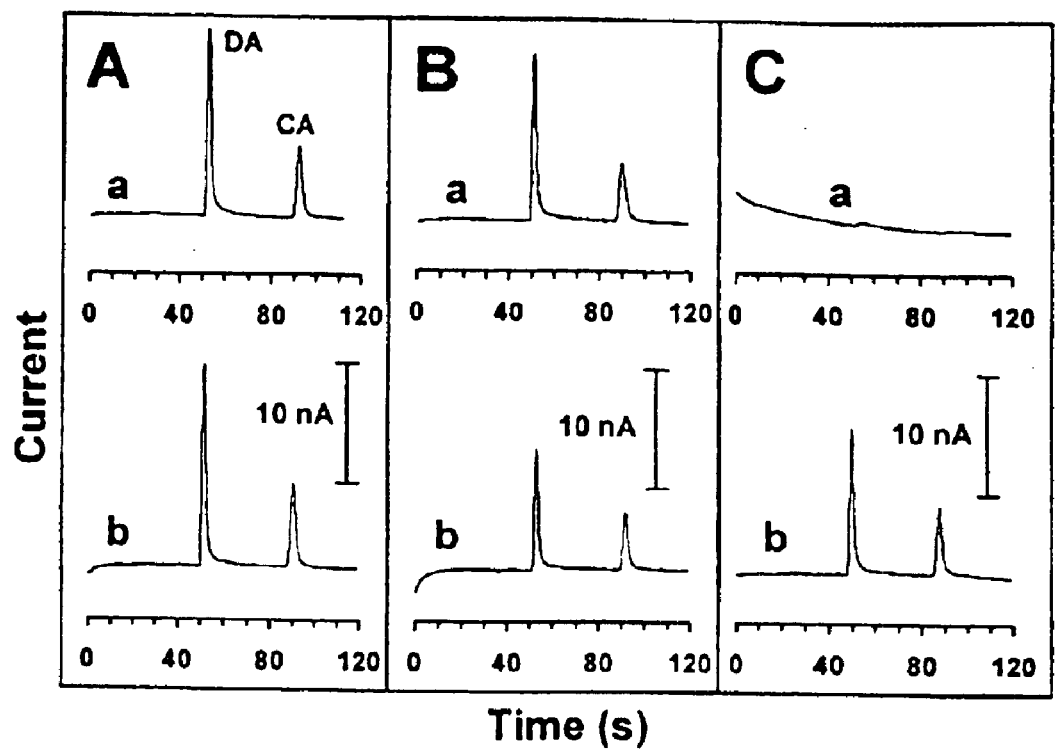
FIG. 5 is a plot of the influence of different carbon inks for the screen-printed carbon electrode on detection of different analytes.

FIG. 5(a) displays electropherograms for an equimolar (100 $\mu$M) mixture of dopamine (DA) and catechol (CA) using detectors based on the Ercon (A), Acheson (B), and ESL (C) carbon inks of Example 1, and a separation voltage of +1500 V, using the device of Examples 1 and 2 and the methods of Example 3. MES buffer (25 mM, pH 6.5) was used as the electrophoresis buffer, with sample injection at +1000 V for 2 seconds and detection at +0.70 V using a 60 $\mu$m spacing between the electrode surface and the channel outlet. The Ercon and Acheson based working electrodes resulted in well-defined, sharp and resolved peaks, a flat baseline, and favorable signal-to-noise characteristics. No response is observed using the ESL working electrode (C(a)). Anodic activation, often used for enhancing the electrochemical reactivity of thick-film detectors, offered a dramatic improvement of the response of the ESL-based detector (C(b)). Such treatment yields no further enhancement of the signals observed with the Ercon and Acheson electrodes (A and B (b)). Ercon-based thick-film detectors were selected for subsequent use as described in Examples 5 and following.

EXAMPLE 5

Separation Voltage Influence

Figure 6:
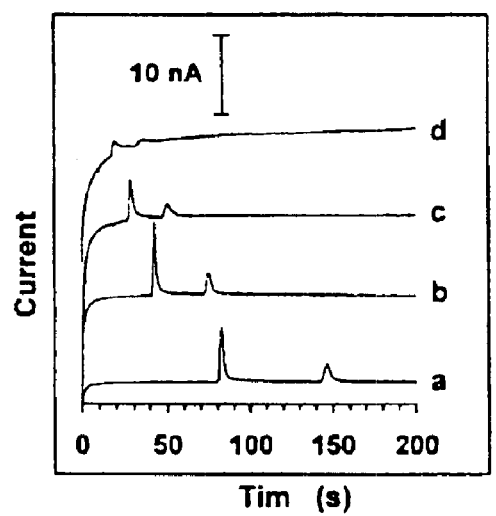
FIG. 6 is a plot on the influence of separation voltage on detection of different analytes.

FIG. 6 examines the influence of the separation voltage upon the response (using a 60 $\mu$m spacing between the channel outlet and the electrode surface) of the device of Examples 1 and 2, using the methods of Example 3, for detection of 100 $\mu$M dopamine and catechol. The separation efficiency, the current signals, and baseline slope were affected by the separation voltage. Increasing the voltage from +1000 to +4000 V (in 1000 V steps, a–d) dramatically decreased the retention times for both analytes. The largest amperometric signals were observed using the +2000 V separation, while the +4000V separation results in small peaks over a sloping baseline. The data of FIG. 6, particularly the initial charging-current baseline rise, indicates incomplete isolation from the higher separation voltages. The separation voltage has a small effect upon the background noise.

EXAMPLE 6

Effect of Spacing on Response

Figure 7:
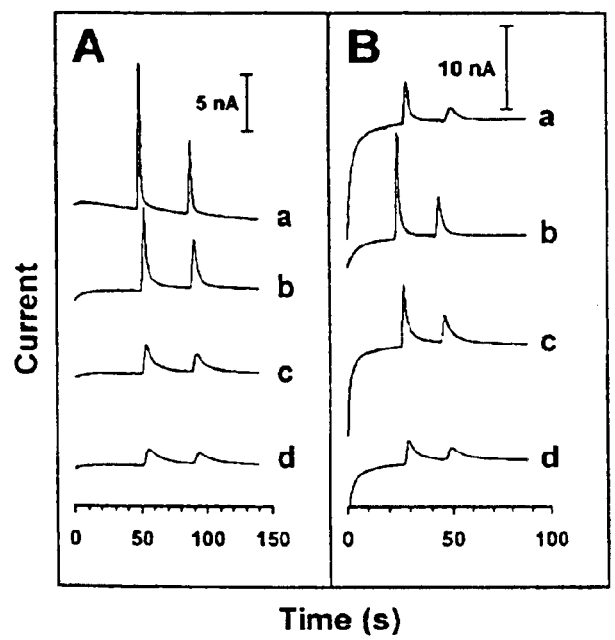
FIG. 7 is a plot on the influence of the distance between the channel outlet and the screen-printed working electrode upon the response at two different separation voltages.

FIG. 7 depicts the effect of spacing of the distance between the channel outlet and the screen printed working electrode on the response for 100 μM dopamine and catechol using separation voltages of +1500 (A) and +3000 V (B) with the device of Examples 1 and 2 and the general methods of Example 3. The screen-printed strip was separated from the channel outlet by a distance of (a) 60, (b) 120, (c) 180 and (d) 240 μm. Using +1500 V separations, the amperometric signal decreased dramatically (−10 fold) upon increasing the spacing between 60 and 240 μm (a–d, A). The spacing also influenced the separation efficiency, as indicated from the decrease in the number of theoretical plates, from 4400 to 130 (for dopamine) and from 4100 to 490 (for catechol) between 60 and 240 μm, respectively. Such change in the separation efficiency reflects increased postcapillary diffusional broadening at large channel-electrode distances. Longer channels can be used for improving the separation efficiency. The peak broadening at the larger spacing is coupled to a slight increase in the retention times, from 49 to 55 seconds (for dopamine) and from 88 to 94 seconds (for catechol) between 60 and 240 μm. A different trend was observed using the +3000V separations, for which the 120 μm spacing yielded the largest signals, shortest retention times, and highest separation efficiency (b,B). The number of theoretical plates (for dopamine) were 830, 2010, 950, and 200 for the 60, 120, 180, and 240 μm distances, respectively. This trend may be attributed to spacing affecting decoupling from the separation voltage (with improved isolation at larger distances), as well as the fluid mass transport at the detector surface. The capillary-detector spacing had a negligible effect upon detector noise.

EXAMPLE 7

Changes in Detection Potential

Figure 8:
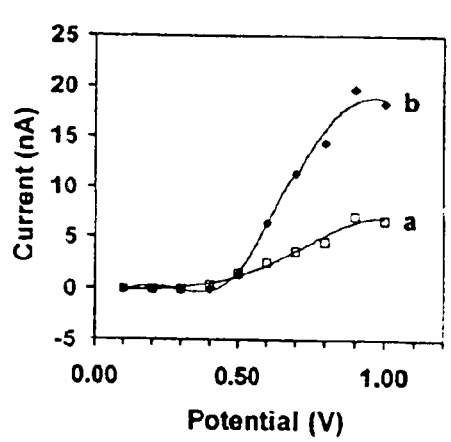
FIG. 8 is a hydrodynamic voltammogram of two different analytes.

FIG. 8 depicts hydrodynamic voltammograms for the oxidation of 100 μM catechol (a) and 100 μM epinephrine (b) with the device of Examples 1 and 2 and the general methods of Example 3. The curves were taken stepwise, in conjunction with a 1500 V CE separation, by making 100 mV changes in detection potential. Neither compound displayed any response below +0.40 V. The response rose gradually between +0.50 and +0.90 V, after which it leveled off. The half-wave potentials are +0.66 V (epinephrine) and +0.69 V (catechol). Such drawn out voltammograms reflect the resistance of the printed carbon composite surface. Subsequent amperometric detection work employed a potential of +0.70 V that offered the best signal-to-noise characteristics. A dramatic increase in the baseline current, its slope, and the corresponding noise was observed at higher potentials. A 100 mV anodic shift of the waves and ~50% enhancements of the limiting current were observed upon increasing the separation voltage from 1500 to 3000 V.

EXAMPLE 8

Analytical Performance

Figure 9:
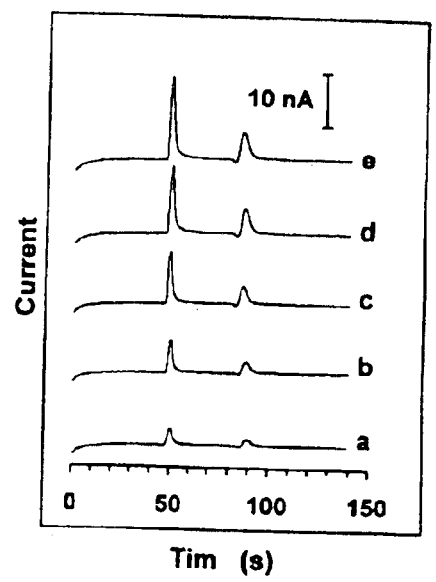
FIG. 9 is an electropherogram for different concentrations of analytes.

The thick-film electrochemical CE detector displayed well-defined concentration dependence. Electropherograms for sample mixtures containing increasing levels of dopamine and catechol in $2 \times 10^{-5}$ M steps are shown In FIG. 9(a–e) using the device of Examples 1 and 2 and the general methods of Example 3. The sample mixtures contained 20 (a), 40(b), 60 (c), 80 (d) and 100 (e) μM catechol and dopamine. Defined peaks proportional to the analyte concentration were observed for both compounds. The resulting calibration plots were linear with sensitivities of 0.160 and 0.0610 nA/μM for dopamine and catechol, respectively (correlation coefficients, 0.998 and 0.989). Combining the high sensitivity of the thick-film detector with its low noise level results in low detection limits of $3.8 \times 10^{-7}$ dopamine and $7.8 \times 10^{-7}$ M catechol, respectively, based on the signal-to-noise characteristics (S/N=3) of the response to a mixture containing $2 \times 10^{-8}$ M of these compounds.

EXAMPLE 9

Reproducibility

The high sensitivity and speed of the CE/thick-film detector system was found to be highly reproducible. A series of 20 repetitive injections using the device of Examples 1 and 2 and the general methods of Example 3 of a 50 μM dopamine solution, using the same detector strip, gave a mean value of 7.4 nA and a relative standard deviation of 4.3%. Different detector strips also displayed a good precision. The design of the microsystem permitted rapid 5–10 second replacement of the detector strip.

EXAMPLE 10

Explosives Detection

Figure 10:
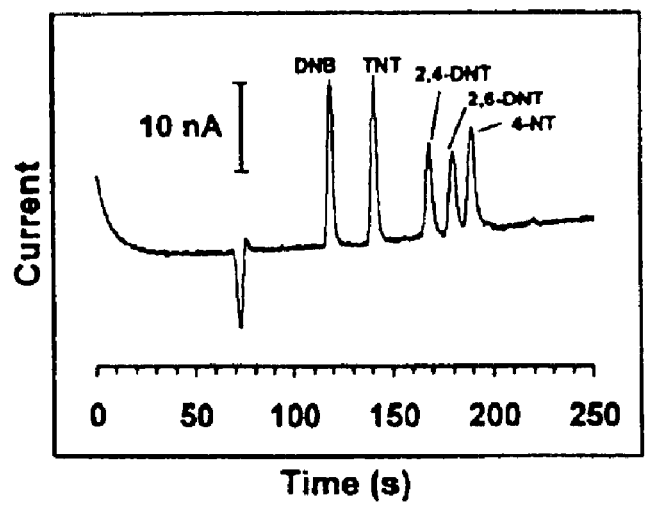
FIG. 10 is an electropherogram for multiple different analytes.

FIG. 10 demonstrates the utility of the CE/electrochemical system for analyzing a mixture of common nitroaromatic explosives with the device of Examples 1 and 2 and the general methods of Example 3. The inherent redox activity of nitroaromatic explosives makes them ideal candidates for electrochemical detection. Amperometric detection has been employed previously for measuring nitroaromatic explosives following their conventional CE separations, but not for microscale on-chip analysis. The microchip explosive analysis was performed with a borate buffer (15 mM, pH 8.7) containing 25 mM SDS. The electropherogram of FIG. 10 shows rapid separation and detection of five explosive compounds. (DNB, 2,4-DNT, 2,6-DNT, 4-NT and TNT, each at 10 mg/L except for 4-NT, which was at 20 mg/L), in a total time of approximately 3 minutes using a separation potential of +1500 V and 60 μm spacing between the detector and channel outlet. Despite the negative potential (−0.70 V) required to reduce the nitro moiety, the thick-film electrochemical detector displayed low background noise and sharp peaks for these 10–20 mg/L concentrations. The signal-to-noise characteristics resulted in low detection limits ranging from 0.6 mg/L (for DNB and TNT) to 2.0 mg/L (for 4-NT; S/N=3), a detectability limit and speed consistent with on-site security and environmental needs.

EXAMPLE 11

Preparation of Palladium-Deposited Detector for Hydrazine Compounds

A chip-based CE/amperometric system for the separation and detection of hydrazine compounds was constructed. Because of the toxicological significance of hydrazine compounds, a reliable method is required for their environmental and industrial monitoring. The screen-printed electrodes were printed with a semiautomatic printer again using Acheson ink Electrodag 440B was used for printing electrode strips as described in Example 2. The palladium-modified screen-printed electrode was prepared by scanning (cycling) the potential between +0.6 and −0.6 V (vs. Ag/AgCl wire) for 60 cycles in a 0.5 M HCl solution containing 1000 ppm Pd(VI).

EXAMPLE 12

Electrophoresis Protocol for Separation and Detection of Hydrazine Compounds

An apparatus as in Examples 1 and 11, with the Palladium-deposited detectors of Example 11, was used. Prior to use, the channels were treated by rinsing with 0.1 M sodium hydroxide and deionized water for 20 and 5 minutes respectively. The buffer and sample reservoirs in the chip holder and the corresponding pipette tips on the microchannel chip were filled with 200 µL of buffer and sample solutions, respectively. The chip was then placed in the chip holder with the pipette tips pointing downwards into the reservoirs, while the detection reservoir filled with buffer solution. Finally, the high-voltage power supply was connected to the reservoirs. A voltage of +1000 V was applied for 30 seconds to the sample reservoir with the detection reservoir grounded and the buffer reservoir floating, in order to facilitate the filling of the injection channel (between the separation channel and the sample reservoir).

The electrophoresis buffer was a phosphate buffer solution (10 mM, pH 7.3) containing 1 mM potassium chloride. Prior to use, the buffer solutions were filtered through a 0.45 µm filter (Gelman Acrodisc) and sonicated for 20 minutes. The injection was performed by applying +500 V to the sample reservoir for 3 seconds with the detection reservoir grounded and the buffer reservoir floating. The separation was performed by applying +1000 V to the buffer reservoir with the detection reservoir grounded and the sample reservoir floating.

EXAMPLE 13

Retention of Hydrazines

Figure 11:
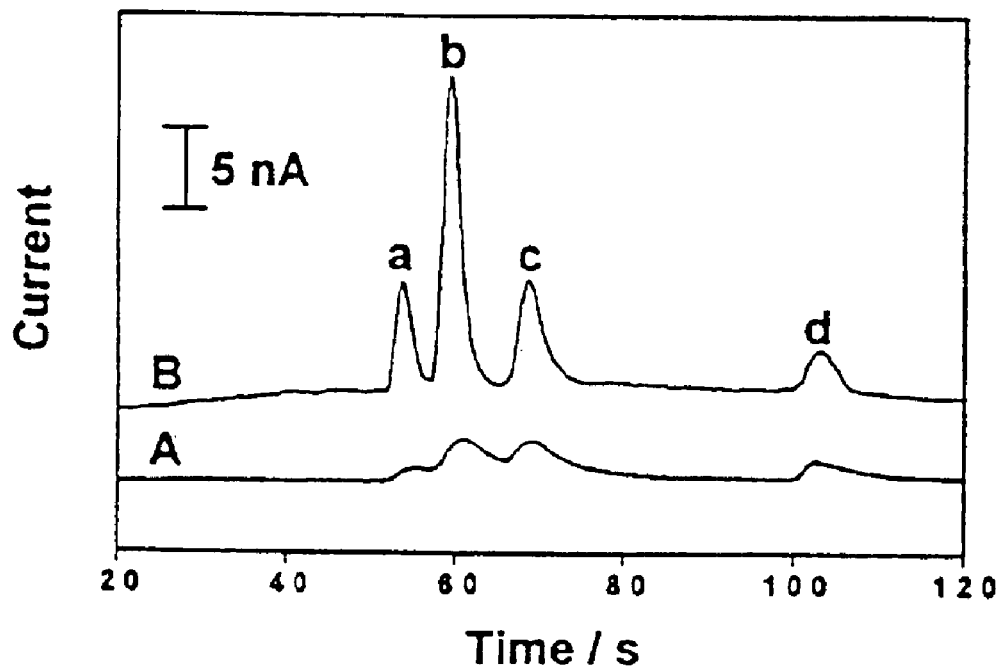
FIG. 11 is an electropherogram for different analytes obtained with a bare and palladium-modified screen-printed working electrode.

Using the apparatus of Examples 1 and 11 and the protocol of Example 12, a series of compounds were analyzed. FIG. 11 compares electropherograms obtained at the bare (A) and palladium-coated (B) carbon strip detectors for a mixture containing 50 µM hydrazine (a), 100 µM methylhydrazine (b), 300 µM dimethylhydrazine (c), and 150 µM phenylhydrazine (d). The injection potential was +500 V, separation potential +1000 V, and detection potential +0.5 V for (B) and +0.8 V for (A). Phosphate buffer (10 mM and pH 7.3) was used as running buffer.

Despite significantly lower operating potential (+0.50 vs. +0.80 V for the bare electrode), the palladium-modified electrode resulted in substantially larger and sharper peaks. The four peaks were well-resolved, with the entire assay requiring less than 2 minutes, with hydrazine, methylhydrazine, and dimethylhydrazine detected within less than 75 seconds; an even faster separation, 20 to 30 seconds, was achieved using higher separation voltages. The data of FIG. 11 illustrate the advantages of using catalytic-modified electrode detectors for detecting high overvoltage analytes. The flat baseline and low noise level also indicate an effective isolation from the high separation potential.

EXAMPLE 14

Hydrodynamic Voltammograms for Hydrazine and Methylhydrazine

Figure 12:
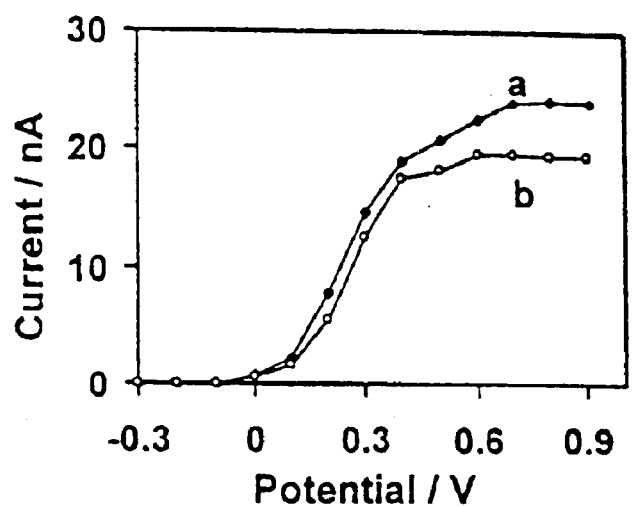
FIG. 12 is a hydrodynamic voltammogram of two different analytes.

The marked decrease in the overpotential for the detection of the hydrazine compounds is illustrated from the voltammetric profiles of FIG. 12, obtained using the apparatus and methods as in Example 13. The figure depicts typical hydrodynamic voltammograms for the oxidation of 100 µM hydrazine (a) and methylhydrazine (b). The curves were developed pointwise by making 100 MV changes in the applied potential over the −0.3 to +0.9 V range, and using a separation voltage of 1000 V. Both compounds display similar current-potential profiles, with defined waves, starting around +0.0 V, and leveling off above +0.5 V. The half-wave potentials are +0.26 V. All subsequent amperometric work employed a potential of +0.5 V.

EXAMPLE 15

Influence of Separation Potential on Hydrazine Compounds

Figure 13:
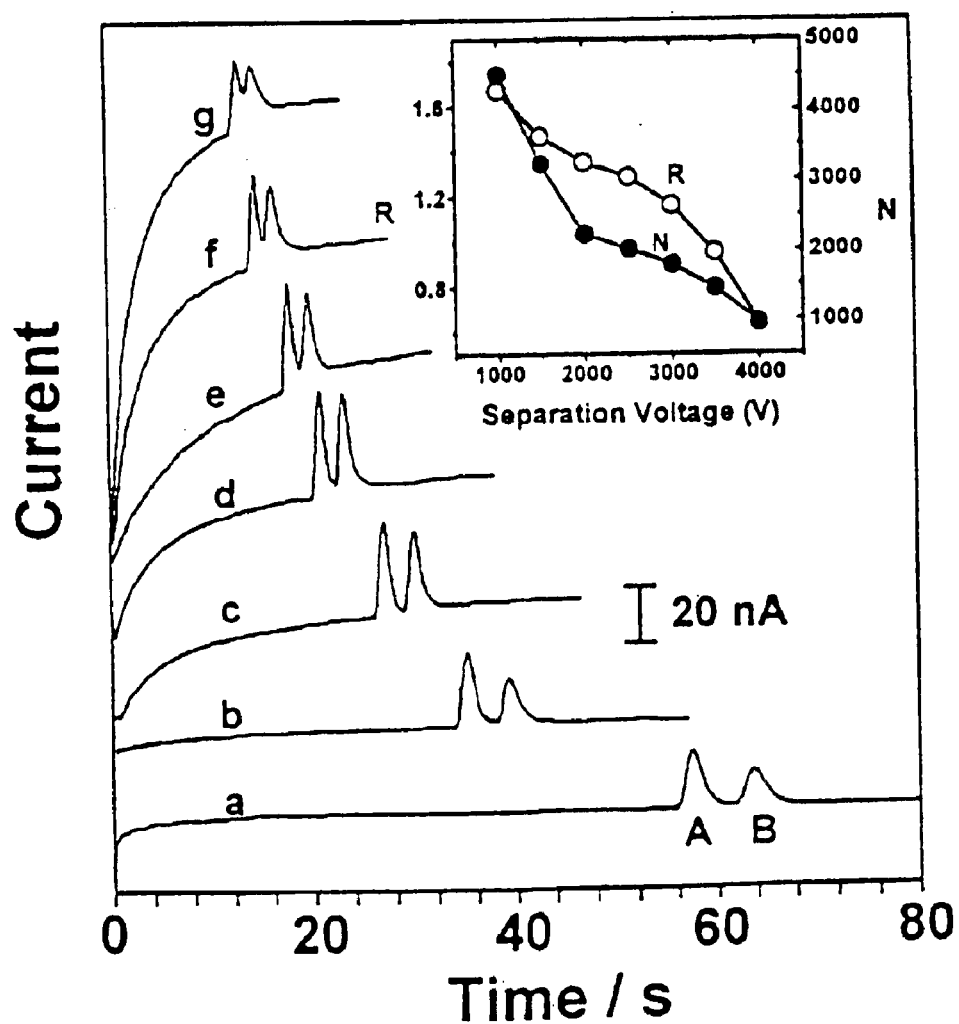
FIG. 13 is a plot of the influence of the separation voltage on the response at different separation voltages, with an insert showing the effect of separation potential on the resolution and number of apparent theoretical plates for hydrazine.

The effect of the separation potential upon the amperometric response and separation efficiency is shown in FIG. 13. The mixture contained 100 µM hydrazine (A) and 300 µM dimethylhydrazine (B). Separation was performed using (a)+1000 V, (b)+1500 V, (c)+2000 V, (d)+2500 V, (e)+3000 V, (f)+3500 V, and (g)+4000 V. Other conditions, as in Example 13. Also shown (inset) is the effect of separation potential upon the resolution (R) and number of apparent theoretical plates (N) for hydrazine. As expected, increasing the separation potential from 1000 to 4000 V (in 500 V increments, a–g) dramatically decreased the migration time for both hydrazine (A) and methylhydrazine (B), from 57 to 13 seconds and from 64 to 15 seconds respectively. The hydrazine peak width (at half height) decreased from around 3.1 seconds at 1000 V to about 1.8 seconds at 4000 V. Also shown (as inset) is the effect of the separation voltage upon the separation efficiency, i.e., on the plate number (N for hydrazine) and the resolution (R). The plate number decreases rapidly (from 4550 to 2230) upon raising the voltage between 1000 V and 2000 V; a slower change in the plate number (between 2230 and 950) was observed over the 2000 V to 4000 V range. The resolution between the hydrazine and methylhydrazine peaks decreased from 1.65 to 0.61 upon raising the separation voltage between 1000 V and 4000 V. The peak currents increased rapidly with the voltage between 1000 V and 2500 V and decreased slowly at higher voltages. Such a decrease can be attributed to the anodic shift of the hydrodynamic voltammogram that results in operation below the potential-independent transport-limited plateau region. The separation voltage had a negligible effect upon the background noise level. Flat baselines were observed using the low separation voltages; however, a larger initial baseline slope was observed for voltages ranging from 2500 V and 4000 V, indicating an incomplete isolation from high separation voltages.

EXAMPLE 16

Concentration Dependence of Detection of Hydrazines

Figure 14:
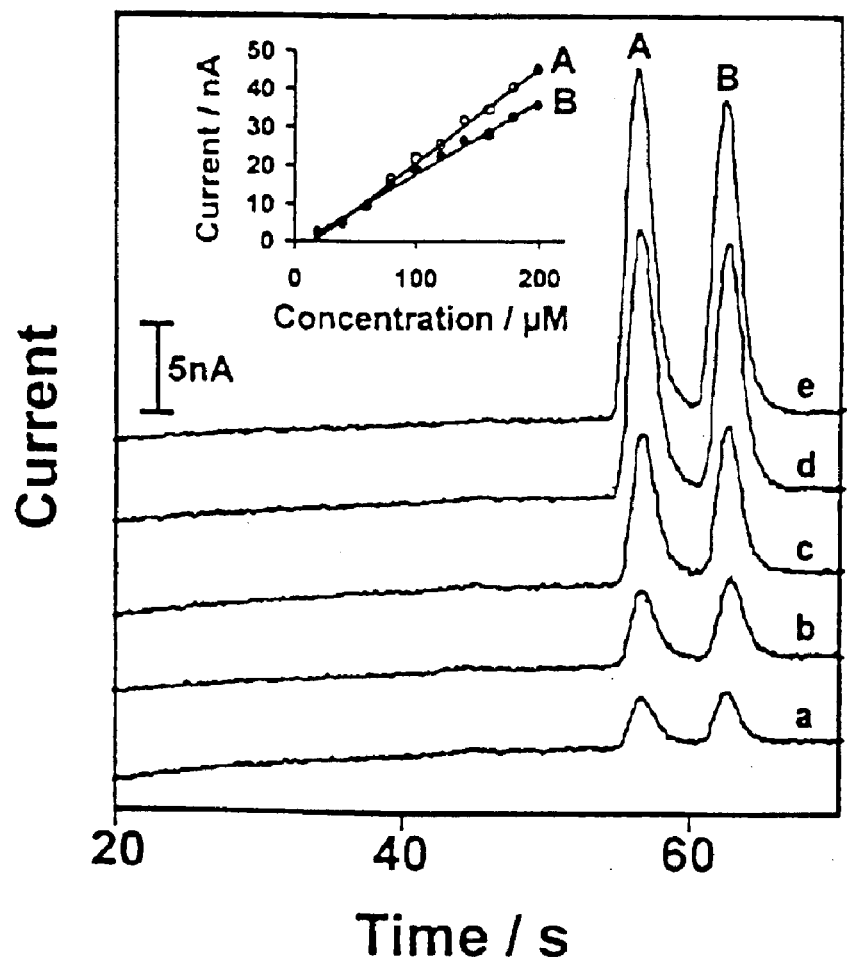
FIG. 14 is an electropherogram for different concentrations of analytes, with an insert showing resulting calibration plots over a specified concentration range.

Electropherograms for sample mixtures containing increasing levels of hydrazine and methylhydrazine in $2 \times 10^{-5}$ M steps are shown in FIG. 14, which depicts results for mixtures containing (a) 20, (b) 40, (c) 60, (d) 80, and (e) 100 µM hydrazine (A) and methylhydrazine (B), again using conditions as in Example 13. Also shown (inset) are the resulting calibration plots over the 20 µM to 200 µM range. Defined peaks proportional to the analyte concentration were observed for both compounds. The resulting calibration plots (also shown) were linear with sensitivities of 0.247 and 0.188 nA/µM for hydrazine and methylhydrazine, respectively (correlation coefficients, 0.998 and 0.996). The high sensitivity of the modified-electrode detector is coupled to a low noise level that resulted in low detection limits of $1.5 \times 10^{-5}$ M hydrazine and $1.6 \times 10^{-5}$ M methylhydrazine, respectively based on the signal-to-noise characteristics (S/N=3) of the response to a mixture containing $1 \times 10^{-5}$ M of these compounds, not shown. Such values are similar to those common for electrochemical detection to conventional fused-silica capillary electrophoresis.

A series of 6 repetitive injections of a mixture containing 100 $\mu$M hydrazine and methylhydrazine (using the same detector strip) resulted in relative standard deviations of 2.0 and 7.7%, respectively. Different detector strips also displayed a good precision, as expected for the thick-film microfabrication and the reproducible detector positioning.

EXAMPLE 17

Gold-Coated Electrode for Phenolic Compound Detection

An electrode was made as generally described in Example 2, with the carbon working-electrode area coated with gold by applying a pulse wave-form with a square-wave pulse potential between −0.2 and +0.75 V, versus Ag/AgCl, with a pulse width of 0.6 seconds for 30 minutes in a solution containing 300 ppm Au(III), 0.1 M NaCl, and 1.5% HCl. Electrophoresis and detection proceeded as in Example 3, with a mixed borate/phosphate buffer, 10 mM each (pH 8.0), for separating chlorophenols or a 10 mM borate buffer (pH 10.5) for other phenols, using the device of FIG. 3. A potential of +1500 V was applied to the sample reservoir 36 for 20 seconds to fill the injection channel, between the separation channel 20 and the sample reservoir 36, while the detection reservoir was grounded and all the other reservoirs floating. The injection was effected by applying +1500 V between reservoir 36 and the grounded detection reservoir for 2 seconds. This drove the sample "plug" into the separation channel through the intersection. Reservoir 32 was not used and was filled with buffer to provide equal hydrostatic levels. Separations were performed by switching the high voltage contacts and applying separation potential of +1500 V to the running buffer reservoir 34 with the detection reservoir grounded and all other reservoirs floating.

Figure 15:
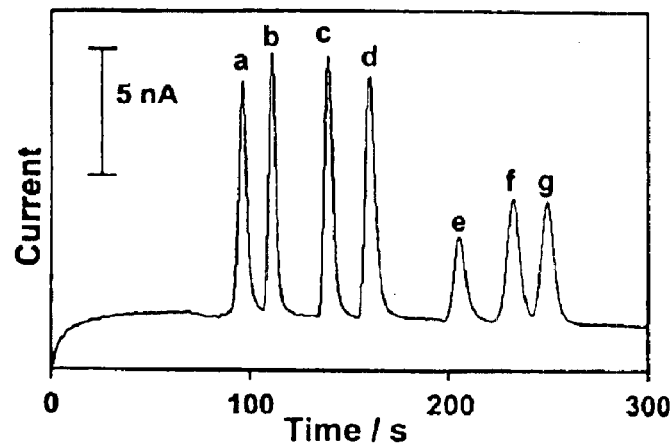
FIG. 15 is a plot of the separation and detection of phenol and six chlorophenols.

FIG. 15 depicts an electropherogram obtained at the gold-coated carbon strip detectors for a mixture containing (a) 100 $\mu$M phenol; (b) 100 $\mu$M 2-chlorophenol; (c) 200 $\mu$M 2,4-dichlorophenol; (d) 200 $\mu$M 2,3-dichlorophenol; (e) 200 $\mu$M 2,4,5-trichlorophenol; (f) 200 $\mu$M 2.4,6-trichlorophenol; and (g) 200 $\mu$M 2,6-dichlorophenol. The raw data of electrophorograms were digitally filtered by 35-point least-square smoothing. The seven peaks were well resolved, with the entire assay requiring around 4 minutes. Analogous measurements with conventional fused silica CE capillaries required significantly longer periods, over 15 minutes. The migration order reflects the p$K_a$ values of the individual chlorophenols. The flat baseline and low noise level at this separation potential indicate an effective isolation from the high separation potential, even in the absence of a decoupling mechanism. These, along with the well-defined response peaks, indicate convenient quantitation down to the micromolar level.

EXAMPLE 18

Detection of Other Phenolic Compounds

Figure 16:
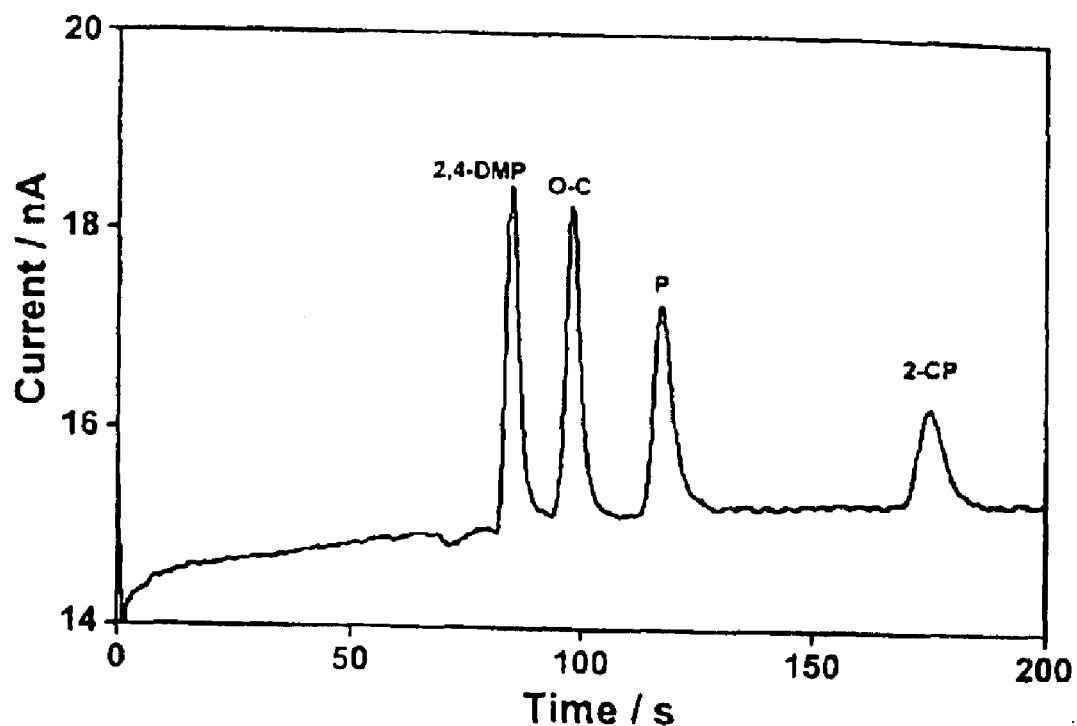
FIG. 16 is a plot of the separation and detection of different analytes.

FIG. 16 depicts separation and detection of phenolic compounds with high p$K_a$ values and 10 mM borate buffer at pH 10.5 and a separation potential of +0.9 V. Other conditions are as in Example 17. Complete separation of $6 \times 10^{-5}$ M 2,4 dimethylphenol (2,4 DMP), o-cresol (O—C), phenol (P), and 2-chlorophenol (2-CP) was obtained within 3 minutes.

EXAMPLE 19

Phenol Oxidation at Electrodes Over Potential Range

Figure 17:
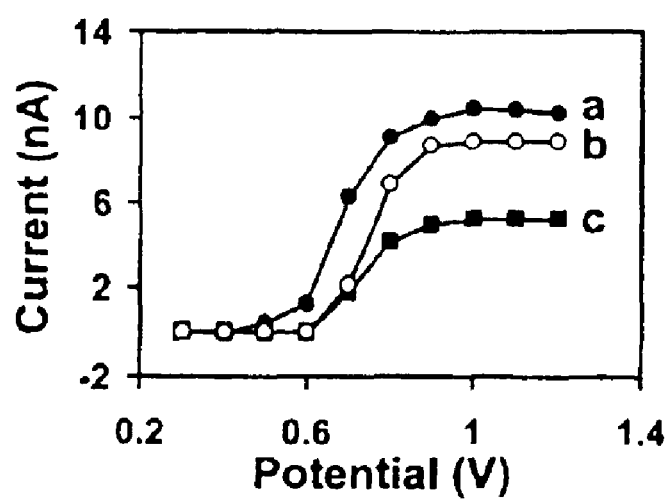
FIG. 17 is a hydrodynamic voltammogram of three different analytes.

FIG. 17 depicts hydrodynamic voltammograms of (a) $1 \times 10^{-4}$ M phenol; (b) $1.5 \times 10^{-4}$ M 2.4-dichlorophenol; and (c) $3 \times 10^{-4}$ M 2,4,5-trichlorophenol, with operating conditions as in Examples 17 and 18. The curves were developed pointwise by making 100 mV changes in the applied potential over the +0.3 V to +1.20 V range, and using a separation voltage of 1500 V. A well-defined sigmoidal response is observed for all three compounds. The waves start at (a)+0.50 V or (b)+0.80 V and level off above (b)+0.90 V or (a,c)+1.0 V. The half-wave potentials are (a)+0.69 V, (b)+0.76 V and (c)+0.75 V.

EXAMPLE 20

Figure 18:
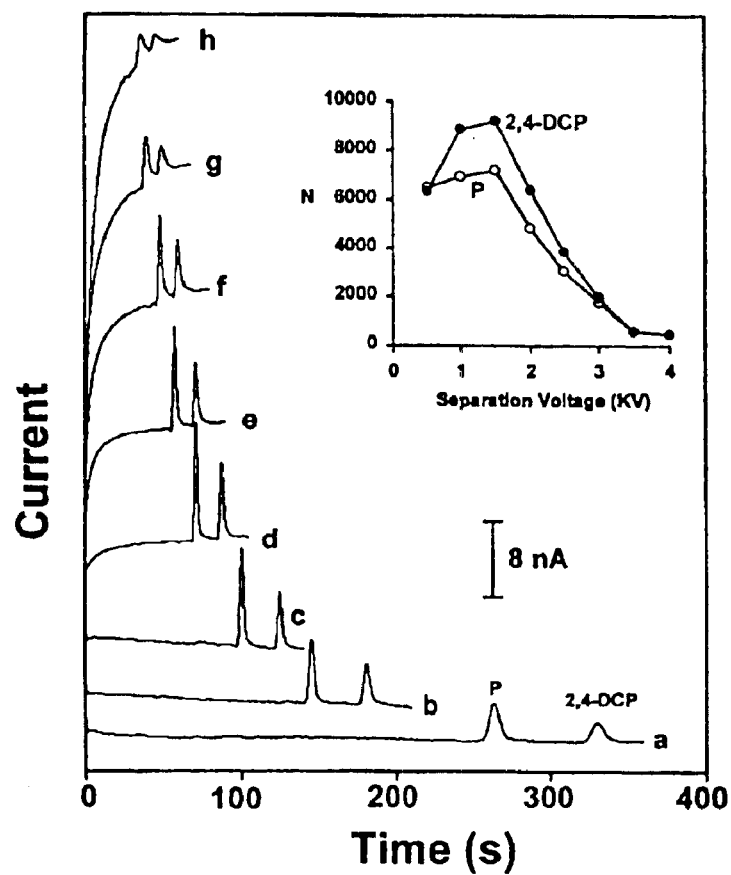
FIG. 18 is a plot of the influence of separation voltage on the response for an analyte at different separation voltages, with an insert showing the effect of separation voltage on the number of apparent theoretical plates for one analyte.

Effect of Separation Potential on Amperometric Response and Separation Efficiency for Phenolic Compounds FIG. 18 depicts the influence of the separation voltage upon the response for a mixture containing $1 \times 10^{-4}$ M of phenol and 2,4-dichlorophenol. Separation was performed using (a)+500 V; (b)+1000 V; (c)+1500 V; (d)+2000 V; (e)+2500 V; (f)+3000 V; (g)+3500 V; and (h)+4000 V, with other conditions as in Examples 17 and 18. Increasing the separation potential from 500 to 4000 V (in 500 V Increments, a–h) dramatically decreased the migration time for both phenol (P) and 2,4-dichlorophenol (2,4-DCP), from 265 to 30 seconds and from 330 to 45 seconds, respectively. The phenol peak width (at half height) decreased from around 8.5 seconds at 500 V to about 5.5 seconds at 4000 V. Also shown (as inset) is the effect of the separation voltage upon the separation efficiency, i.e. on the plate number (N). For both phenol and dichlorophenol the plate number increased to maximum values of 7200 and 9100, respectively, upon raising the separation potential between 500 and 1500 V, and decreases gradually (to 400) upon raising the potential to 3500 V. The maximum number of plates (9100) corresponds to a plate height of 0.0079 mm. The separation voltage had a negligible effect upon the background noise level. Flat baselines were observed using the low separation voltages (<2000 V); however, a larger initial baseline slope is observed for voltages ranging from 2000 to 4000 V, Indicating an incomplete isolation from high separation voltages.

EXAMPLE 21

Concentration Dependent Detection

Figure 19:
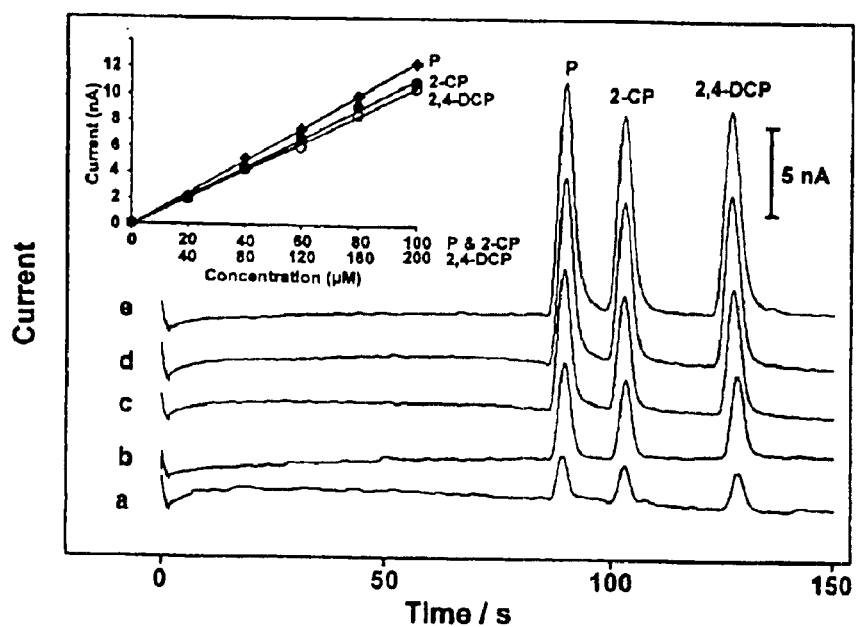
FIG. 19 is a plot of calibration data, including electropherograms for mixtures containing increasing levels of analytes and an insert showing the resulting calibration plots.

FIG. 19 depicts eletropherograms for mixtures containing increasing levels of phenol and 2-chlorophenol in $2 \times 10^{-5}$ M steps and of 2,4-dichlorophenol in $4 \times 10^{-5}$ M steps (a–e). Also shown (inset) are the resulting calibration plots. Defined peaks proportional to the analyte concentration were observed for all three compounds. The resulting calibration plots (also shown) were highly linear with sensitivities of 124.3, 11.6 and 52.6 nA/mM for phenol, 2-chlorophenol, and 2,4-dichlorophenol, respectively (correlation coefficients, 0.999, 0.998 and 0.999). Highly linear calibration plots in the range of 0–200 $\mu$M, with sensitivities of 25, 11.4, 12.8, 12.2, 51.8 and 54.2 nA/mM, were obtained also for 2,3-dichlorophenol, 2,4,5-trichlorophenol, 2,4,6-trichlorophenol, o-cresol and 2,4-dimethylphenol, respectively (with correlation coefficients, 0.999, 0.985, 0.998, 0.998 and 0.999), over the $1\times10^{-4}$–$1\times10^{-5}$ M range.

Figure 20:
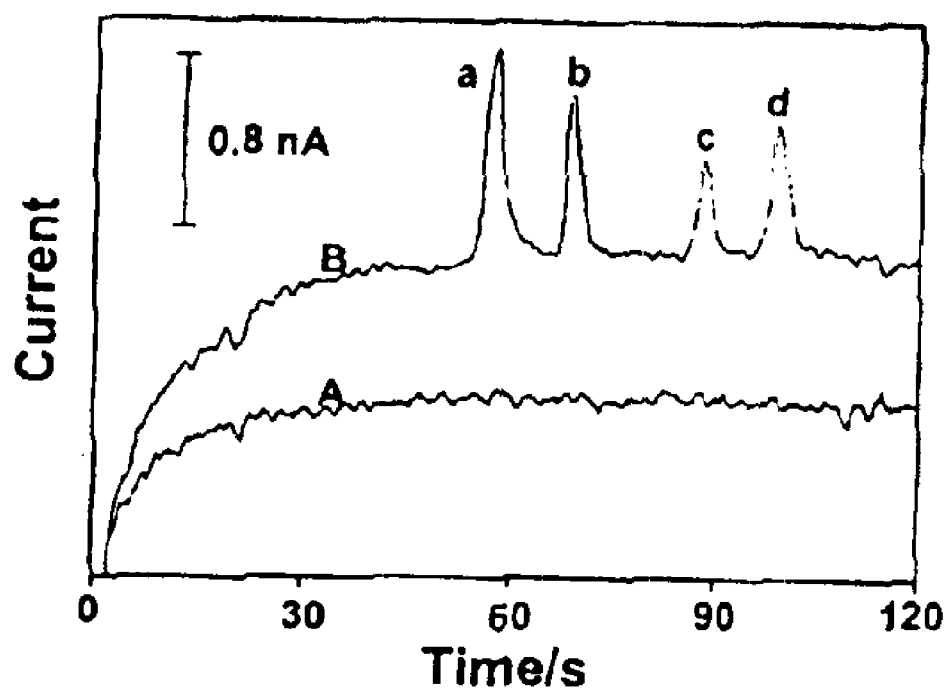
FIG. 20 is an electropherogram for river water samples before and after the addition of phenolic compounds.

FIG. 20 depicts an electropherogram for a river water sample, before (A) and after (B) spiking with (a) $1\times10^{-5}$ M phenol, (b) 2-chlorophenol, (c) 2,4-dichlorophenol, and (d) 2,3-dichlorophenol. Plot (B) was characterized with four well-defined and baseline-resolved peaks. The total assay time was around 100 seconds. The favorable signal-to-noise characteristics of these real-sample data indicate low detection limits of about $1\times10^{-4}$ to about $2\times10^{-6}$ M (based on S/N=3).

EXAMPLE 22

Lack of Surface Fouling with Phenolic Compounds

Amperometric detection of phenols is commonly prone to surface fouling, due to formation of inhibitory polymeric films. Using the methods of Examples 17 to 21, no surface fouling or passivation was observed. A series of 20 repetitive injections of a $6\times10^{-5}$ M phenol solution (using the same detector strip) resulted in a relative standard deviation (R.S.D.) of 3.7%. Similarly, a R.S.D. of 6.2% was observed for 12 successive measurements of $6\times10^{-5}$ M 2,4 dimethylphenol. The other phenolic compounds were also subjected to repetitive injections and resulted in R.S.D. values of 3.2, 3.1, 5.4, 5.5, 3.7, 5.3, and 6.6 for 2-chlorophenol, 2,4-dichlorophenol, 2,3-dichlorophenol, 2,4,5-trichlorophenol, 2,4,6-trichlorophenol, 2,6-dichlorophenol, and o-cresol respectively. Such high stability is attributed to the use of extremely small sample volumes that result in a negligible accumulation of reaction products.

EXAMPLE 23

Separation Reaction Device for Simultaneous Bioassays

A glass microchip layout as depicted in FIG. 4 was employed for bioassays of glucose, ascorbic acid, uric acid, and acetaminophen using a glucose oxidase (GOx) enzyme system. The sample and the enzyme GOx are mixed; the neutral glucose substrate and hydrogen peroxide are then separated by electrophoresis from the anionic urate and ascorbic species, which migrate at a slower rate, as depicted in the schematic diagram of FIG. 21.

In the device of FIG. 4, the enzyme (GOx)/running buffer and sample solutions are mixed at the channel intersection and in the separation channel using electrokinetic flow. The enzymatic reaction occurs along the separation/reaction channel while the enzyme (in the running buffer) and glucose (in the sample plug) diffuse downstream:

glucose +oxygen $\xrightarrow{GOx}$ hydrogen peroxide+gluconic acid

Figure 21:
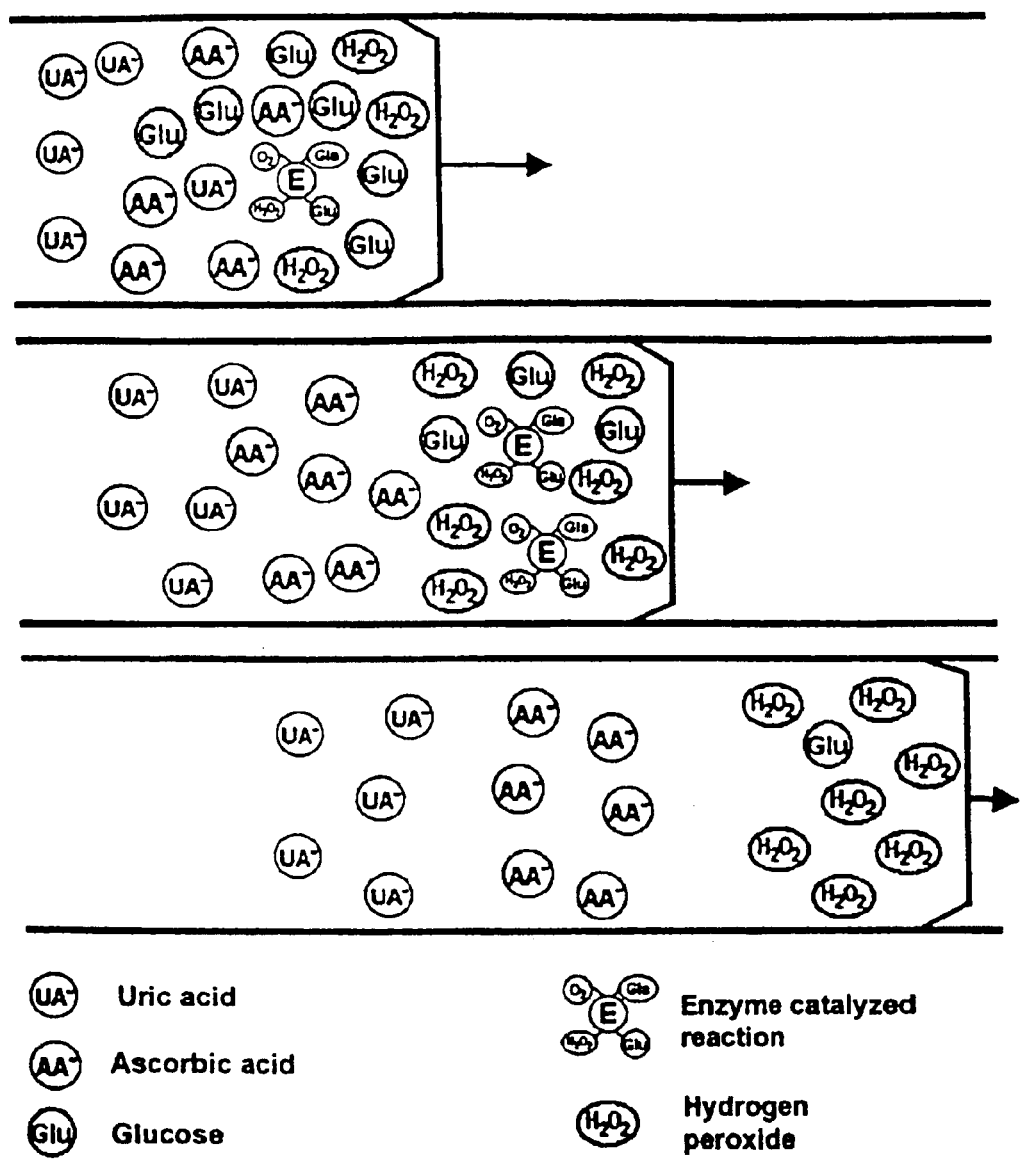
FIG. 21 is a schematic diagram depicting enzymatic and separation processes along a separation channel.

The enzymatically liberated neutral peroxide species is electrophoretically separated from the anionic uric and ascorbic acids in the separation/reaction channel, see FIG. 21, and the three oxidizable species are detected at the downstream working electrode at different migration times.

EXAMPLE 24

Simultaneous Bioassay Electrophoresis Procedures

A gold-coated electrode was used as in Example 17. The channels of the device of FIG. 4 were treated before use by rinsing with 0.1 M sodium hydroxide and deionized water for 20 and 5 min, respectively. To perform the separation, the buffer reservoir was filled with the phosphate buffer solution, while the buffer-with-GOx reservoir was filled with phosphate buffer containing 75 U/mL glucose oxidase. The sample reservoir was filled with mixtures containing glucose, uric add, ascorbic acid, and/or acetaminophen. The detection/waste reservoir was filled with the phosphate buffer solution. Other reservoirs were filled with 200 $\mu$L of the corresponding solutions, thus maintaining equal hydrostatic levels. The initial filling of the injection channel (between the separation channel and the sample reservoir) with the sample solution was achieved by applying a potential of +1500 V for 20 seconds to the sample reservoir with the detection reservoir grounded and other reservoirs floating.

The actual assays were performed by loading the sample plug into the separation/reaction channel, by applying +1500 V to the sample reservoir for 2 seconds (with the detection reservoir grounded and other reservoirs floating). Subsequently, for simultaneous measurements of glucose, uric acid, and ascorbic acid, the separation voltage was applied to the buffer-with-GOx reservoir. Mixing of the glucose substrate (in the sample plug) with the enzyme (in the running buffer) started at the intersection and proceeded primarily down in the separation channel. The neutral hydrogen peroxide species (produced in the separation/reaction channel) and the uric and ascorbic acids were separated in the separation/reaction channel of FIG. 4, and the three oxidizable species were detected amperometrically at different migration times.

Alternatively, measurements of glucose and acetaminophen were carried out by comparing the responses with and without the enzyme. For this purpose, a total signal was measured with the running buffer containing GOx, while the acetaminophen signal alone was recorded by applying the separation voltage to the buffer reservoir (containing no GOx). The current difference was used for quantifying the glucose concentration in the sample mixture. The electropherograms were recorded with a time resolution of 0.1 seconds while the detection potential was applied (usually +0.9 V vs Ag/AgCl wire). Sample injections were performed after stabilization of the baseline. No software filtration of the signal was used. All bioassays were carried out at room temperature.

EXAMPLE 25

Simultaneous Bioassay Electrophoresis Results

Figure 22:
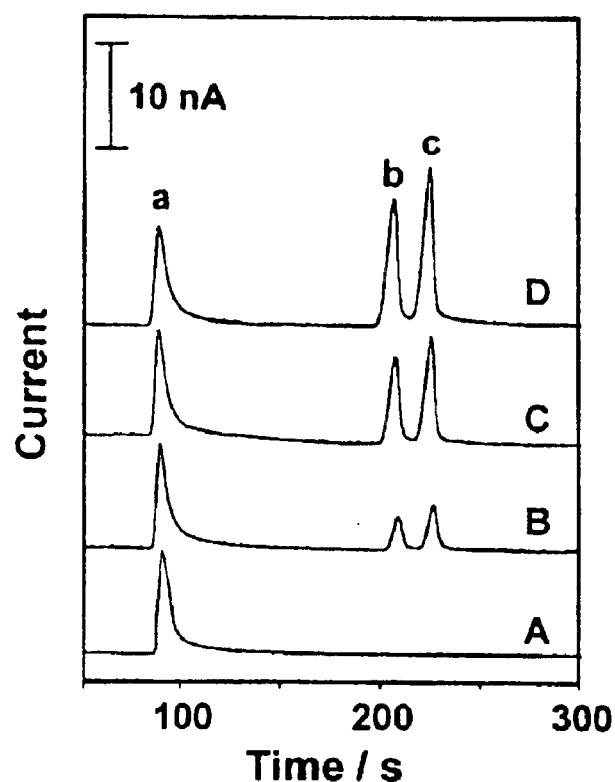
FIG. 22 is an electropherogram for glucose and glucose solutions containing increasing levels of ascorbic acid and uric acid.

Using the device of Example 23 and the procedure of Example 24, electropherograms were obtained for $1\times10^{-3}$ M glucose (a) solutions containing increasing levels of ascorbic acid (b) and uric acid (c) where (A) is glucose alone and ascorbic acid and uric acid is $2\times10^{-4}$ M (B); $5\times10^{-4}$ M (C); $7\times10^{-4}$ M (D), as shown in FIG. 22. Conditions included a running phosphate buffer (10 mM, pH 7.4) solution, containing 75 u/mL GOx; separation potential, +1500 V; injection potential, +1500 V; injection time, 2 seconds; and detection potential, +0.9 V. These electropherograms indicate convenient and rapid separation and detection of all three compounds, with a total time of around 4 minutes using a separation potential of +1500 V. Glucose alone was actually detected within less than 100 seconds. Under these conditions, there was a nearly complete isolation from the high separation potential, as indicated from the flat baseline and low noise level. The increasing levels of ascorbic and uric acids did not affect the glucose response, even at levels that greatly exceed the physiological levels of ascorbate and urate. Note also that the current peaks of ascorbic and uric acids are proportional to their concentrations.

EXAMPLE 26

Acetaminophen Detection

Figure 23:
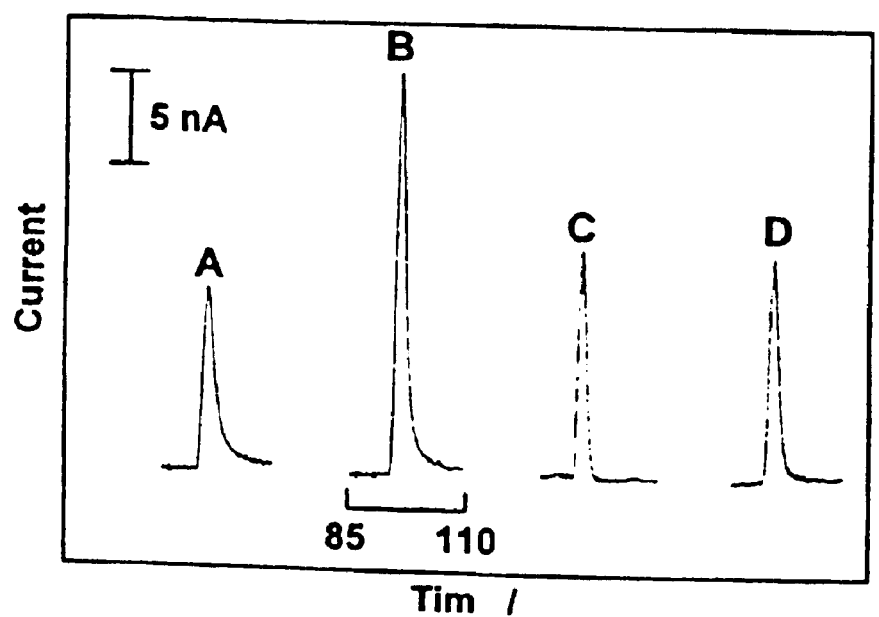
FIG. 23 is a plot of portions of electropherograms showing measurements of glucose and acetaminophen in the presence and absence of glucose oxidase.

Acetaminophen, a common neutral interferent, is carried solely by the electroosmotic flow and cannot be resolved from the neutral glucose/peroxide species. Using the method of Example 24 with the device of Example 23, electropherograms as shown in FIG. 23 were obtained in the presence (A, B, D) and absence (C) of GOx in the running buffer. Sample solutions were (A) $1\times10^{-3}$ M glucose, (B) $1\times10^{-3}$ M glucose and $1\times10^{-4}$ M acetaminophen; and (C, D) $1\times10^{-4}$ M acetaminophen. Selective measurements of glucose in the presence of acetaminophen were performed by comparing the responses in the presence and absence of GOx in the separation buffer (A, B, D vs. C). Well-defined peaks with identical migration times (~100 seconds) were observed for glucose (A) and acetaminophen (D) using the GOx-containing buffer; a mixture of the two compounds thus yielded the expected additive response (B). As expected, glucose was not detected in the absence of GOx (not shown); accordingly, only an acetaminophen contribution was observed for the glucose/acetaminophen mixture (C). The glucose signal (in such mixtures) can be readily obtained by the difference in the responses with and without the enzyme (B–C). Notice that this current difference was identical to the current of glucose alone in the presence of GOx (A).

EXAMPLE 27

Effect of Separation Voltages in Simultaneous Bioassays

Figure 24:
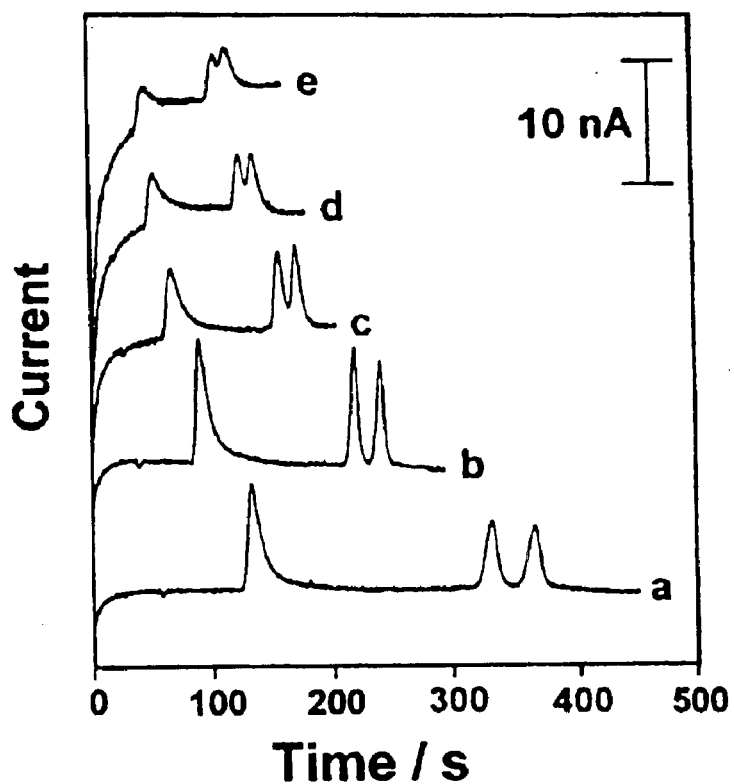
FIG. 24 is a plot showing the effect of separation voltage on glucose and other analytes.

Using the method of Example 24 with the device of Example 23, the influence of the separation potential upon the separation efficiency and overall performance was evaluated. For the results shown in FIG. 24, the sample mixture contained $1\times10^{-3}$ M glucose, $6\times10^{-4}$ M ascorbic acid, and $4\times10^{-4}$ M uric acid. Separation voltages were (a)+1000, (b)+1500, (c)+2000, (d)+2500, and (e)+3000 V. Increasing the separation potential from 1000 to 3000 V (in 500 V increments, a–e) dramatically decreased the migration time for glucose from 135 to 45 seconds. The corresponding times for ascorbic and uric adds were reduced from 330 and 360 to 105 and 115 seconds, respectively. The separation efficiency, represented by the plate number, decreased from 6000 to 1100 (for ascorbic acid) and from 5200 to 1050 (for uric acid) upon raising the separation potential from 1000 to 2500 V. The broader glucose/peroxide peak, associated with the enzymatic reaction, was characterized by smaller plate numbers ranging from 100 (at 2500 V) to 800 (at 1000 V). The relatively low separation efficiency was attributed to the floated injection, used for facilitating the introduction of the anionic species. The separation potential had a negligible effect upon the background noise level. However, a larger initial baseline slope was observed for potentials ranging from 2000 to 3000 V, Indicating an incomplete isolation at high separation potentials. Most subsequent work employed a potential of 1500 V. This separation potential offers convenient glucose measurements within less than 100 seconds. An even faster glucose detection, on a time scale of 1 minute, is expected upon improving the separation efficiency and the injection protocol and/or providing a connection to a precolumn enzymatic reaction.

EXAMPLE 28

Influence of Glucose Oxidase Concentration

Figure 25:
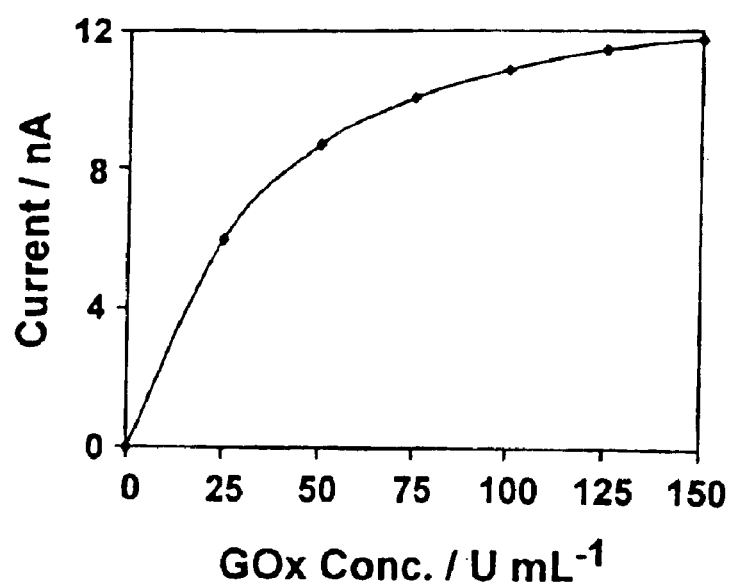
FIG. 25 is a plot of the influence of glucose oxidase concentration on the response to a fixed level of glucose.

Using the method of Example 24 with the device of Example 23, FIG. 25 depicts the effect of the GOx level in the reagent solution upon the response to the $1\times10^{-3}$ M glucose substrate. The current increased rapidly upon raising the GOx concentration between 0 and 50 U/mL, then increased more slowly, and finally started to level off above 125 U/mL. All subsequent work employed 75 U/mL GOx Enzyme levels higher than 100 U/mL resulted in increased background noise and absorption onto the channel walls. Hydrodynamic voltammograms (i.e., plots of current response versus the applied potential) were used for selecting the detector potential. The gold-coated carbon detector displayed a defined wave-shaped voltammogram for glucose, with the current starting at +0.50 V and leveling off above +0.80 V. Most work employed a detection potential of +0.90 V, in view of the high background noise above +1.0 V. The bare carbon surface required higher potentials for the peroxide detection, with the current starting at +0.80 V and a plateau above +1.20 V.

EXAMPLE 29

Run-to-Run Variations in Injection Time

Figure 26:
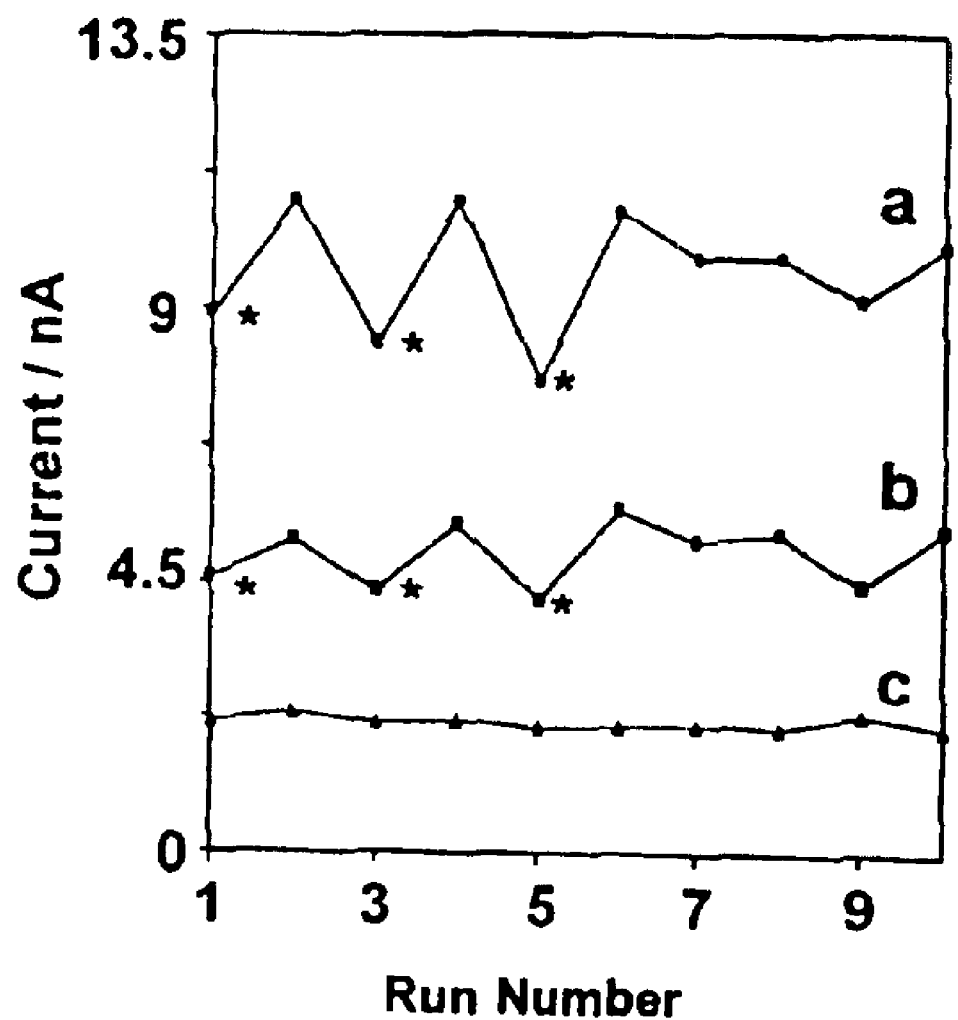
FIG. 26 is a plot of the reproducibility of the current response for glucose and other analytes.

Using the method of Example 24 with the device of Example 23, the run-to-run variation in injection time was evaluated. Results are shown in FIG. 26, which depicts reproducibility of the current response for $1\times10^{-3}$ M glucose (a) and $5\times10^{-4}$ M uric acid (b) and of the glucose-to-uric acid peak ratio (c). Asterisks denote the use of deliberately shorter sample injection times. As shown in FIG. 26, use of uric acid as a "built-in" internal standard greatly improved the reproducibility of repetitive glucose measurements in connection with measurements of the glucose/urate peak ratio. Both the glucose and uric add peaks yielded relative standard deviations of 10.6 and 10.5%, respectively; an R.S.D. of 4.2% was estimated for the glucose/urate peak ratio.

EXAMPLE 30

Concentration Dependence

Using the method of Example 24 with the device of Example 23, electrophoretic peaks for increasing levels of glucose (A), ascorbic acid (B), and uric acid (C) in $1\times10^{-4}$ M steps (a–e), as shown in FIG. 27. Highly linear calibration plots were observed for both ascorbic and uric adds (see insets), with slopes of 21.6 and 21.8 nA/mM (and correlation coefficients r of 0.998 and 0.999, respectively). In contrast and as expected for biocatalytic reactions, the response for the glucose substrate displayed a curvature at concentrations higher than $7\times10^{-4}$ M. A highly linear response was observed for the initial linear portion (slope 17.3 nA/mM; r=0.999). Greater deviations from linearity (above $1\times10^{-4}$ M glucose) have been reported for conventional CE/fluorescence bioassays of glucose. Anal. Chem., 1997, 69, 1326. While conventional biosensors rely on mass-transport-limiting membranes for extending the linear range, biochips should rely on simple dilution for imparting wider dynamic ranges in connection with biocatalytic assays. Sample dilution could thus be readily integrated (with an additional channel to control dilution). The on-chip $K_m$ value, estimated from the corresponding Lineweaver-Burk plot, $6\times10^{-3}$ M, is lower than the value ($2.6\times10^{-2}$ M) reported for GOx in solution. J. Biol. Chem., 1967, 242, 994.

EXAMPLE 31

Apparatus and Protocol with Pre-Column Reactor

Measurements of amino acids were made utilizing pre-column reactions of amino acids with o-phthaldialdehyde (OPA)/2-mercaptoethanol to generate electroactive derivatives that were separated electrophoretically and detected at the end-column electrochemical detector. Using this apparatus and protocol, rapid (6 minute) simultaneous measurements of eight amino adds, down to about $2.5 \times 10^{-6}$ M (5 fmol) level, with linearity up to the $2 \times 10^{-4}$ M level, were made, with good reproducibility. A step of the driving voltage was used for decreasing the migration time of late eluting components and reducing the overall analysis time. Briefly, the device of FIG. 2 was employed, including a reagent reservoir R, a sample reservoir S, a running buffer reservoir RB, and a buffer reservoir B. A reaction chamber RC (200 $\mu$m wide and 3.6 mm long) was connected through 50 $\mu$m wide channels to the reagent and sample reservoirs at one side, and to a four-way injection cross at the other side. The injection cross was followed by a 74 mm long, 50 $\mu$m wide, separation channel. Otherwise, the apparatus was as described in Example 2, with a gold-coated carbon working electrode area as in Example 17.

To perform separations, the reagent reservoir R was filled with 80 $\mu$L of an o-phthalaldehyde (OPA), 2-mercaptoethanol (2ME) reagent solution, while the sample reservoir S was filled with 80 $\mu$L of mixture of amino acids. The two buffer reservoirs B and RB were filled with 70 $\mu$L volume of the electrophoresis buffer. The detection/waste reservoir at the channel outlet side was filled with the electrophoresis buffer solution. A voltage of +1500 V was applied for 60 seconds to the reagent and sample reservoirs with the detection reservoir grounded and other reservoirs floating, in order to fill the reaction chamber and assure a constant mixing ratio. The sample and reagent solutions were loaded electrokinetically into the reaction chamber and mixed together by dispersion. The derivatization reaction of amino acids with OPA occurred in the reaction chamber upon mixing the reagent electrophoresis buffer with the sample, located in the sample reservoir, which produced the OPA-amino acid derivative during the path flowing through the chamber.

The reaction-product "plug" was loaded into the separation channel by applying +1500 V to both sample and reagent reservoirs for 3 seconds with the detection reservoir grounded and the other reservoirs floating. The injection time of 3 seconds corresponded to an injected volume of 2 nL. Separation was usually performed by applying +2000 V to the running-buffer reservoir with the detection reservoir grounded and the other reservoirs floating. Amperometric signals of different amino acids were detected at the detection reservoir at different elution times.

Different sample/reagent mixing ratios were achieved by placing different resistors (ranging from 0 M$\Omega$ to 90 M$\Omega$) between the +1500 V power-supply terminal and the reagent reservoir, while holding the sample reservoir at +1500 V. The currents flowing through the reagent and sample reservoirs were monitored during sample/reagent loading. The actual mixing ratios of the sample and reagent solutions were calculated based on the ratios of the currents flowing through the reagent and sample arms.

EXAMPLE 32

Electropherograms obtained at the Gold-Coated Carbon Working Electrode

Figure 28:
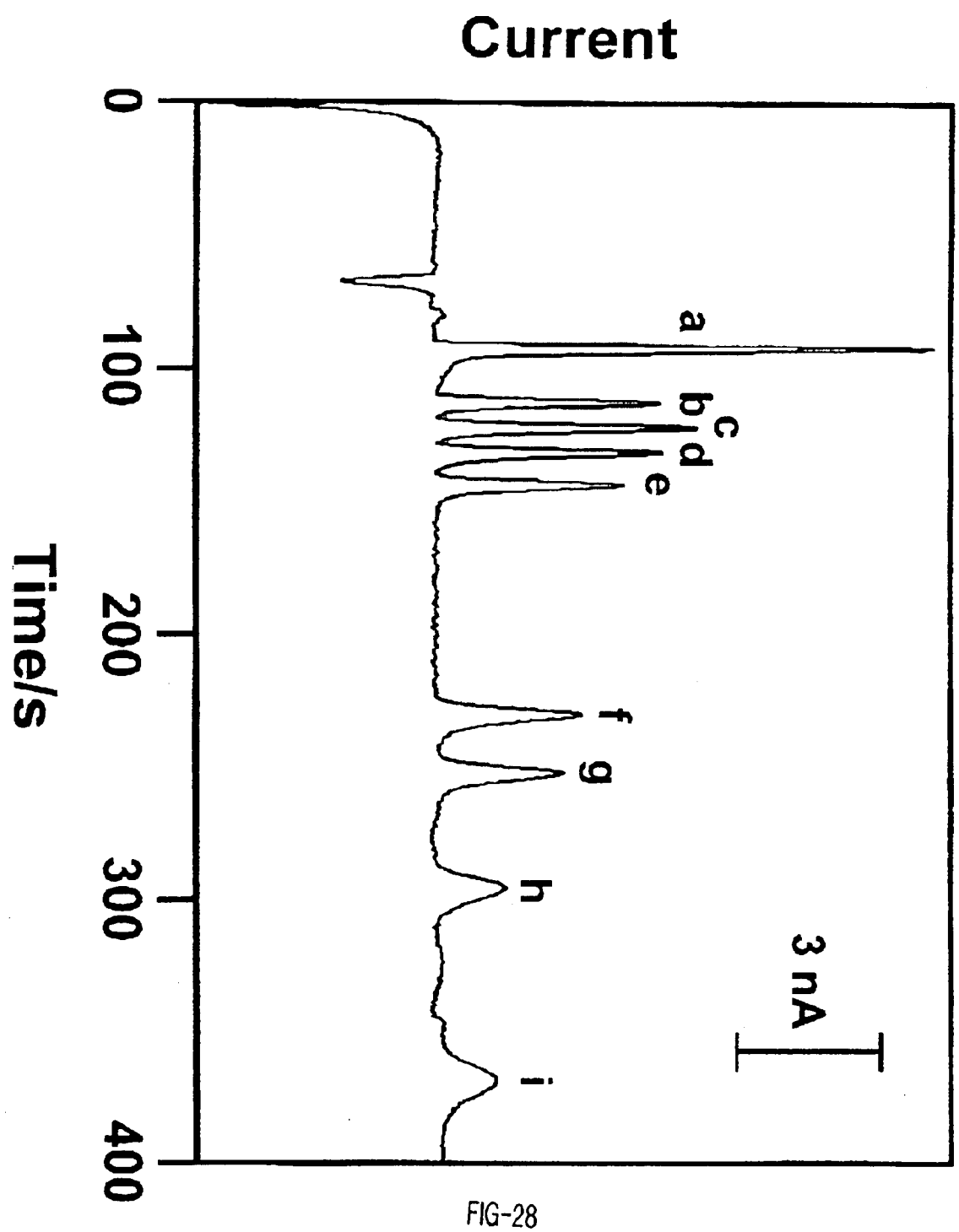
FIG. 28 is an electropherogram for specified amino acids.

Using the device and methods of Example 31, an electrophoresis buffer was made consisting of 20 mM borate buffer containing 30 mM dodecyl sodium sulfate (SDS) at pH 9.4. As shown in FIG. 28, an electropherogram was obtained of a mixture containing $1.0 \times 10^{-4}$ M (b) histidine, (c) valine, (d) isoleucine, (e) leucine, $2.0 \times 10{-4}$ M (f) glutamic acid, (g) aspartic acid, (h) arginine, and (i) lysine, with (a) corresponding to the excess of the 2-ME reagent. An injection potential of +1500 V, separation potential of +2000 V, injection time of 3 seconds, and detection potential of +0.8 V were employed. The reagent solution was $4.8 \times 10^{-3}$ M OPA and $4.2 \times 10^{-3}$ M 2ME. The eight amino acids peaks were well resolved, with the entire assay requiring around six minutes; the first four amino acids are detected within less than three minutes (peaks b–e). The flat baseline and low noise level indicated an effective isolation from the driving voltage.

EXAMPLE 33

Optimization of Separation Using Amino Acids

Figure 29:
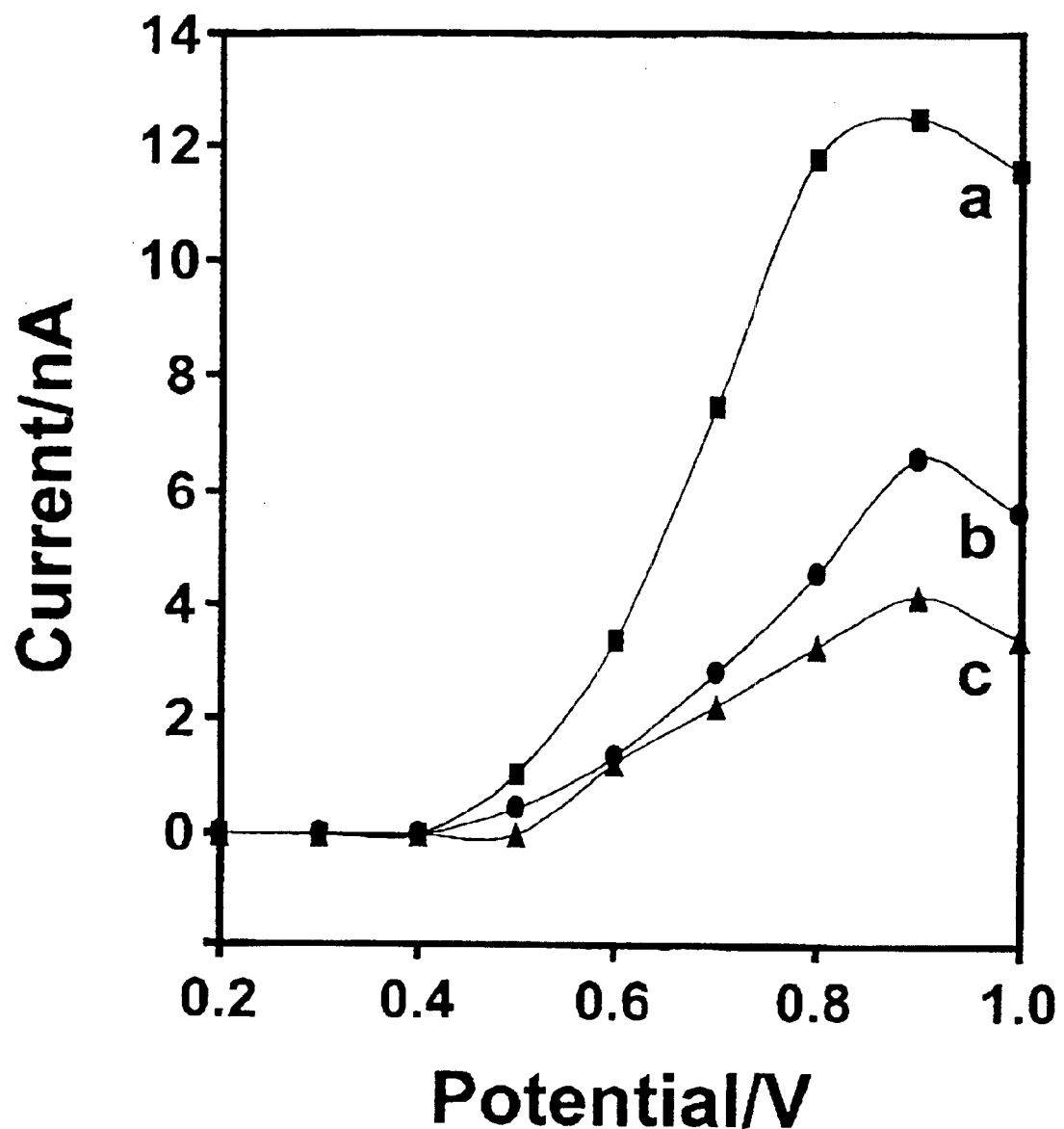
FIG. 29 is a hydrodynamic voltammogram for specified amino adds.

The methods of Example 31 were employed to determine the effect of the detector potential using hydrodynamic voltammograms as shown in FIG. 29. $2 \times 10^{-4}$ M valine (a), glutamic add (b), and arginine (c) were employed, with a reagent solution consisting of $2.4 \times 10^{-3}$ M OPA and $2.1 \times 10^{-3}$ M 2ME. Similar profiles were observed for the three amino acids, reflecting the detection of the corresponding isoindole reaction products. The oxidation started at +0.50 V, with a maximum response observed in the vicinity of +0.90V. Subsequent analytical work was performed with a potential of +0.80 V that offered the most favorable signal-to-background characteristics. The different voltammetric profiles and sensitivity trend (valine>glutamic acid>arginine) of FIG. 29 are related to the chemical structure of the amino-acid residue of the isoindole products.

EXAMPLE 34

Effect of Driving Voltage on Amino Acid Detection

Figure 30:
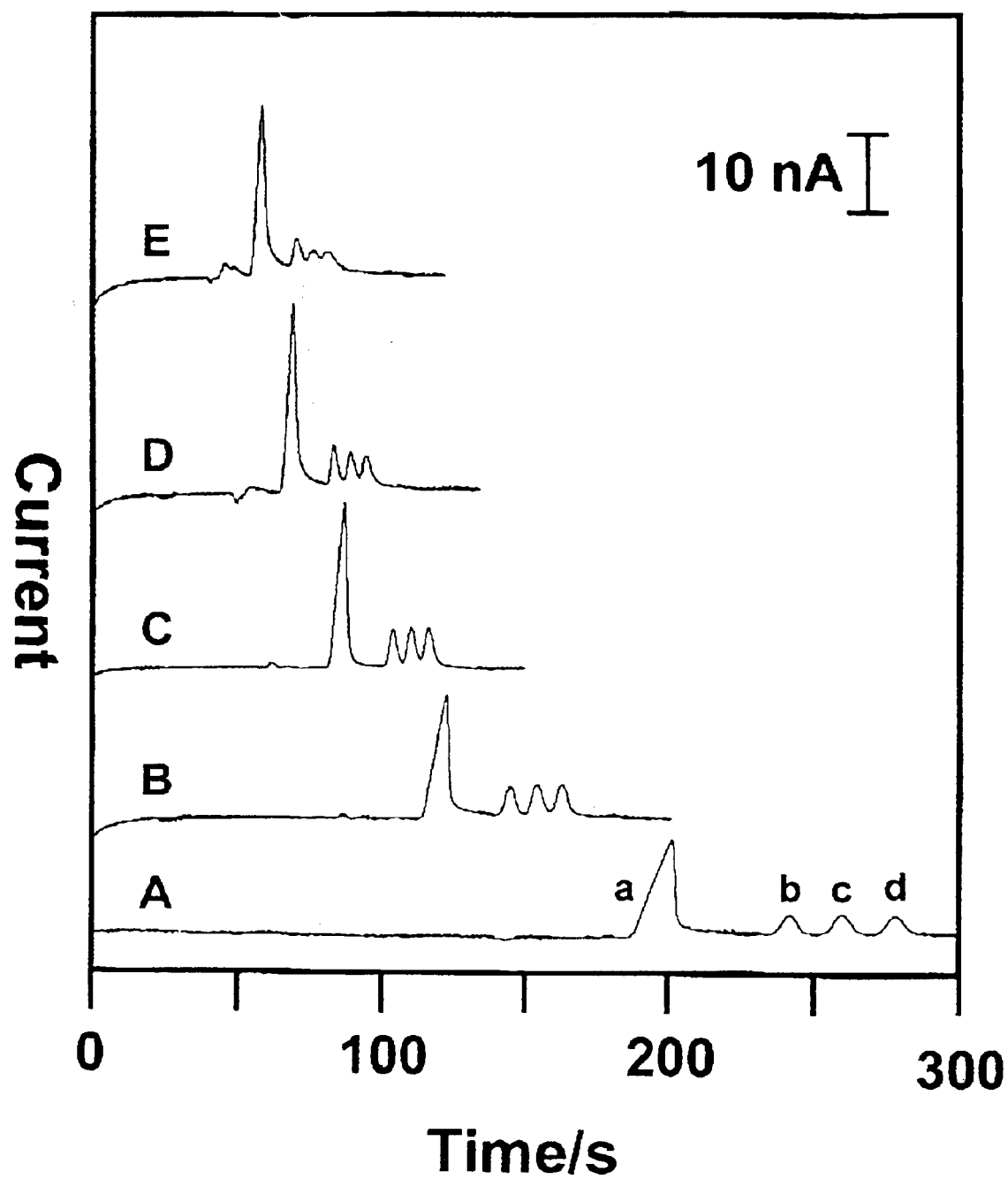
FIG. 30 is a plot of the influence of separation voltage on the response with specified amino acids.

Using the methods of Example 31 the effect of varying the driving voltage is depicted in FIG. 30. $1.5 \times 10^{-4}$ M histidine (b), valine (c) and isoleucine (d) were used, with separations performed using (A)+1000, (B)+1500, (C)+2000, (D)+2500, and (E)+3000 V, and reagent solution consisting of $2.4 \times 10^{-3}$ M OPA and $2.1 \times 10^{-3}$ M 2ME. The increase in the electrical field decreased the migration time for histidine, valine, and isoleucine from 242, 260, and 278 seconds to 70, 76, and 91 seconds, respectively. This decrease is in agreement with the linear dependence between the applied field strength and the migration velocity obtained for all three analytes (not shown). The peak widths at half height also decreased upon increasing the driving voltage, e.g., from 6.1 seconds at 1000 V to about 2.3 seconds at 2500 V in the case of histidine. The decreased separation efficiency at higher fields is indicated from the decrease in the theoretical plate number for histidine from 9,900 at 1000 V to 2900 at 3000 V.

EXAMPLE 35

Stepping of Driving Voltage

Figure 31:
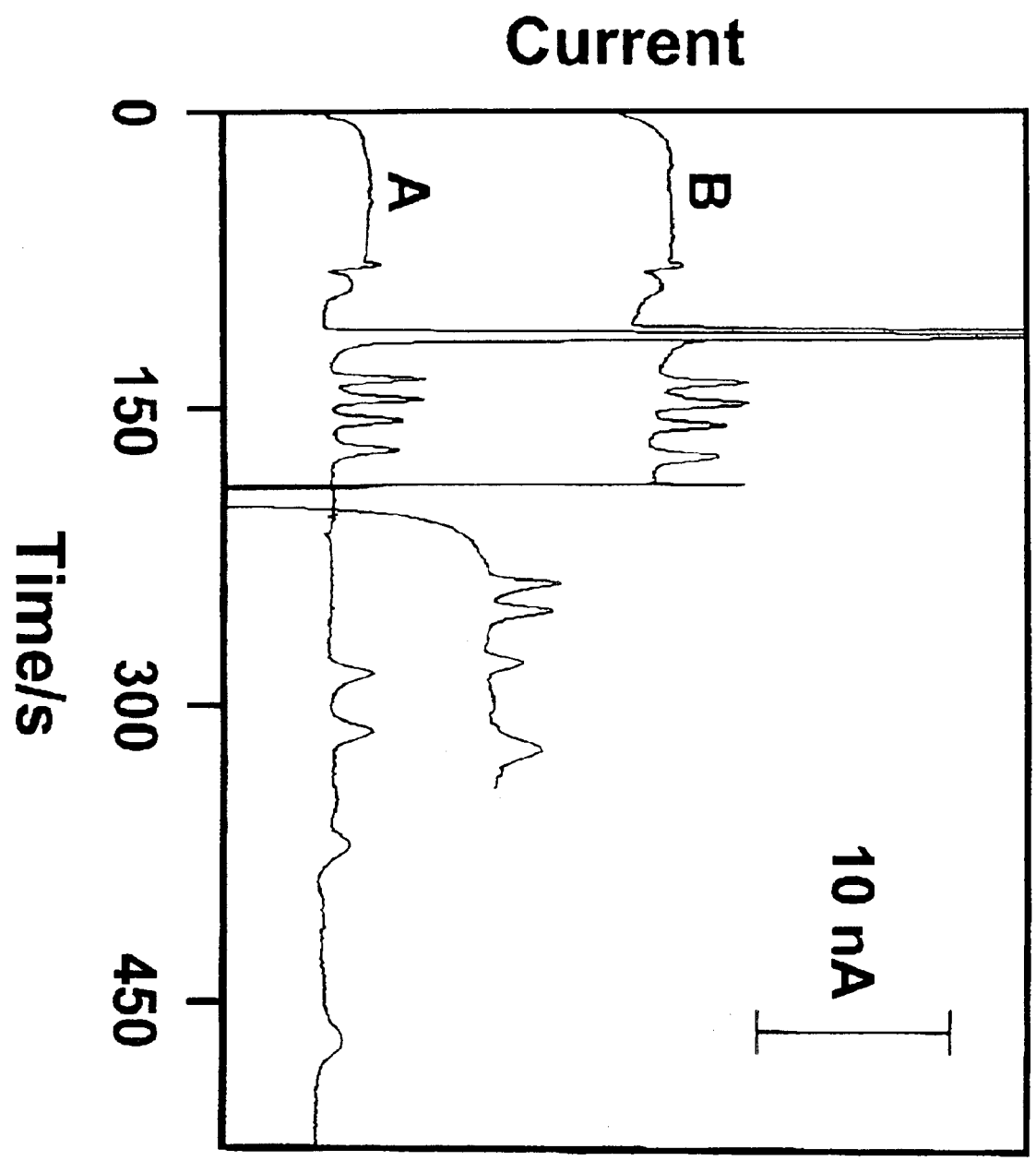
FIG. 31 is an electropherogram for a sample with eight amino acids at altered separation voltages.

Using the methods of Example 31, amino acids of Example 32, and other operating conditions as in Example 33, stepping of the driving voltage for decreasing the migration time of late-eluting components and the overall analysis time was examined. The advantage of stepping the driving voltage, over the use of constant field strength, is demonstrated in FIG. 31. In FIG. 31, (A) depicts constant separation voltage of +1500 V and (B) stepping up the separation voltage to +3000 V after 200 seconds of separation at a separation voltage of +1500 V. By stepping the voltage from +1500 to +3000V, after the initial after 200 seconds, a complete run is accomplished within 320 seconds, rather than the 470 seconds required under a constant field strength, thereby reducing the overall analysis time by about 150 seconds. While the voltage step resulted in an abrupt background noise, the baseline rapidly stabilized to allow convenient quantitation of the late-migrating compounds. As expected, these compounds displayed sharper peaks following the voltage step. In contrast, the use of a constant high voltage of 3000 V resulted in largely overlapping peaks for the early eluting compounds, as shown in FIG. 30(E).

EXAMPLE 36

Changing Ratios of Derivatization Reaction Constituents

Figure 32:
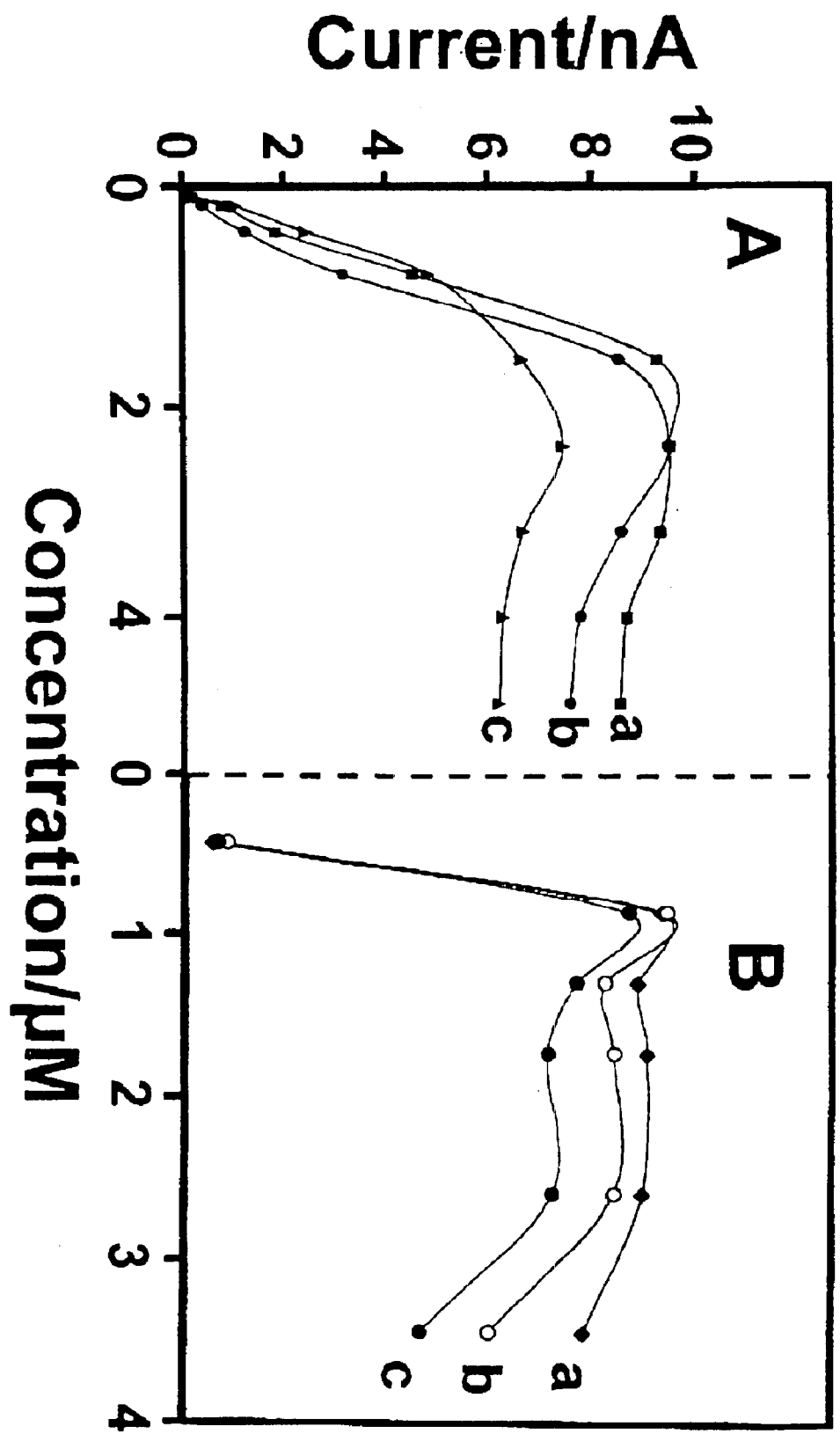
FIG. 32 is a plot of the reactant concentration on the response for a sample mixture of specified amino acids.
Figure 33:
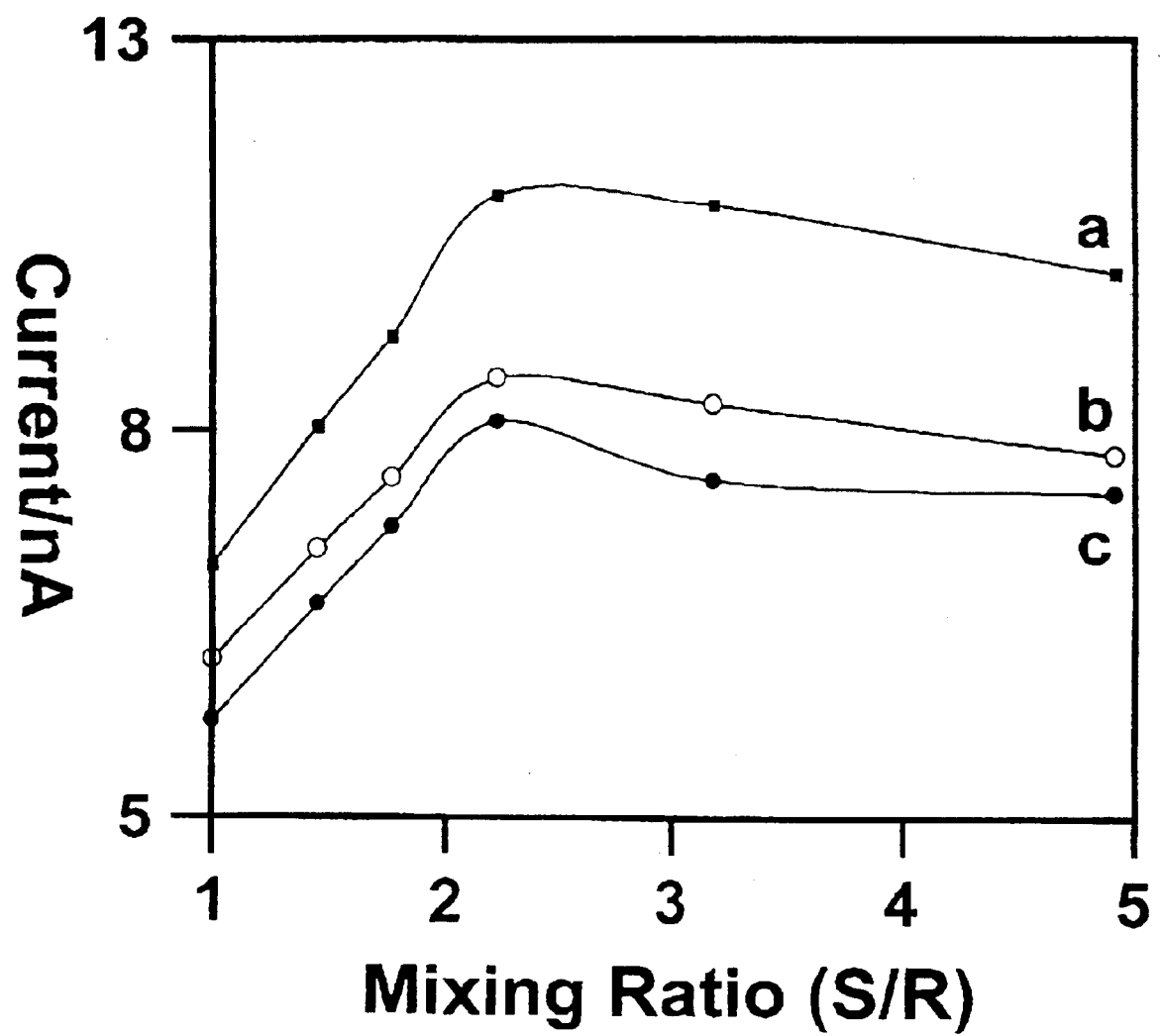
FIG. 33 is a plot of the sample and reactant mixing ratio on the response for specified amino acids.

The derivatization reaction can be altered by controlling the electrical fields in the sample and Reagent arms, and by changing the relative concentrations of the OPA and 2ME reagents. Using the methods of Example 31, the influence of the reagent concentration was examined by varying the concentration of OPA and 2ME with a constant level of the amino acids, as shown in FIG. 32, (A) and (B). The current signals for histidine (a), valine (b), and leucine (c) increased rapidly upon raising the OPA concentration between 0 and $1.6 \times 10^{-3}$ M, and nearly leveled off at higher reagent concentrations (A). The response increased slowly up to $5 \times 10^{-4}$ M 2-mercaptoethanol, than very rapidly to a maximum value around $8 \times 10^{-4}$ M, and decreased slightly at higher levels (B). The maximum reagent concentrations represent a four-fold excess over the amino acid analytes. FIG. 33 displays the effect of the sample/reagent mixing ratio upon the response for a mixture of three amino acids. $2.0 \times 10^{-4}$ M valine (a), isoleucine (b), and leucine (c) were employed, with +1500 V applied to the sample reservoir while the voltage applied to the reagent reservoir was changed from +1390 to +1470 V by placing different resistors between the +1500 V power-supply terminal and the reagent reservoir. The mixing ratio was calculated based on measuring the ratio of currents flowing through the respective reservoirs. For all analytes, the response rose upon increasing the sample/reagent ratio in the reaction chamber from 1.0 to 2.2, after which it decreases slightly.

EXAMPLE 37

Concentration Dependence of Amino Acid Detection

The amperometric detector system and method of Example 31 displayed well-defined concentration dependence. This was examined by recording electropherograms for sample mixtures containing increasing levels of histidine and isoleucine or valine and leucine in ten steps of $2 \times 10^{-5}$ M, with defined peaks, proportional to the analyte concentration, observed for all four compounds. The resulting calibration plots were highly linear with sensitivities of 50.6, 64.1, 41.0, and 59.1 nA/mM for histidine, valine, isoleucine, and leucine, respectively (correlation coefficients, 0.992, 0.999, 0.996 and 0.995). The high sensitivity of the amperometric detector is coupled to a low noise level that resulted in low detection limits of $2.5 \times 10^{-6}$ M for valine and $2.7 \times 10^{-6}$ M for leucine, based on three standard deviations of the noise in assays of a mixture containing $2 \times 10^{-5}$ M of these compounds. Such values correspond to 5.0 and 5.4 fmol valine and leucine, respectively. (i.e., 590 and 710 fg) in the 2 nL injection plugs. Excess concentrations of OPA and 2ME is required to attain such micromolar detection limits, such that the reagent concentration is not limiting the derivatization reaction.

EXAMPLE 38

DNA Detection

The device of Example 1 and methods of Example 3 are employed. A DNA separation matrix is utilized, such as hydroxyethylcellulose. Injection is performed by applying voltage to the sample reservoir for a suitable period of time with the detection reservoir grounded and the buffer reservoir floating. Separation is carried out by applying a separation voltage. Detection is by amperometric means, using an electrode of Example 2.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for conducting a microfluidic process and analysis, said apparatus comprising:
   a first substrate having at least one exterior edge;
   at least one elongated separation channel in the first substrate, the separation channel having an inlet end and an outlet end transiting the at least one exterior edge;
   a fluidic transport means for transport of fluids through the separation channel;
   a second substrate; and
   at least one thick-film electrode for analyte detection on the second substrate, the thick-film electrode being in fluidic connection with the outlet end of the separation channel.

2. The apparatus of claim 1, wherein the fluidic transport means comprises a conductive system in fluidic connection with each end of the separation channel for application of a separation voltage.

3. The apparatus of claim 2, wherein the conductive system comprises electrodes.

4. The apparatus of claim 2, further comprising a high-voltage power supply for application of voltage to the conductive system.

5. The apparatus of claim 1, wherein the fluidic transport means comprises electrokinetic fluid transport.

6. The apparatus of claim 1, wherein the fluidic transport means comprises at least one means elected from the group consisting of electrical, mechanical, centrifugal, magnetic, pneumatic, pressure-activated, and vacuum-activated fluid transport.

7. The apparatus of claim 1, further comprising at least one reference electrode in fluidic connection with the thick-film electrode.

8. The apparatus of claim 1, wherein the first substrate comprises at least one member selected from the group consisting of fused-silica, silica-based, polymer, plastic and elastomer substrates.

9. The apparatus of claim 1, wherein the second substrate comprises at least one member selected from the group consisting of ceramic, polymeric and plastic substrates.

10. The apparatus of claim 1, further comprising an electrical contact to the thick-film electrode.

11. The apparatus of claim 10, further comprising an analyte analysis system in electrical contact with the electrical contact to the thick-film electrode.

12. The apparatus of claim 1, further comprising an analyte analysis system for analyzing an analyte at the thick-film electrode.

13. The apparatus of claim 12, wherein the analyte analysis system comprises an amperometric detection system.

14. The apparatus of claim 13, wherein the amperometric detection system comprises at least one member selected from the group consisting of fixed potential and potential-step amperometric detection systems.

15. The apparatus of claim 12, wherein the analyte analysis system comprises at least one member selected from the group consisting of a stripping potentiometry system and a voltammetric detection system.

16. The apparatus of claim 1, wherein the thick-film electrode is a screen-printed electrode.

17. The apparatus of claim 1, wherein the separation channel has an average bore diameter of from about 1 $\mu$m to about 300 $\mu$m.

18. The apparatus of claim 17, wherein the separation channel has an average bore diameter of from about 20 $\mu$m to about 120 $\mu$m.

19. The apparatus of claim 1, wherein the thick-film electrode has a thickness of from about 1 $\mu$m to about 100 $\mu$m.

20. The apparatus of claim 19, wherein the thickness of the thick-film electrode is between about 8 $\mu$m and 30 $\mu$m.

21. The apparatus of claim 1, wherein the first substrate comprising at least one elongated separation channel is detachable from the second substrate comprising at least one thick-film electrode.

22. The apparatus of claim 21, wherein the first substrate is affixed to the second substrate such that the distance between the thick-film electrode and the outlet end of the separation channel is fixed.

23. The apparatus of claim 22, wherein the distance between the thick-film electrode and the outlet end of the separation channel is from about 1 $\mu$m to about 500 $\mu$m.

24. The apparatus of claim 23, wherein the distance is between about 50 $\mu$m and about 100 $\mu$m.

25. The apparatus of claim 1, wherein the thick-film electrode comprises a carbon ink electrode.

26. The apparatus of claim 1, wherein the thick-film electrode comprises a metal conducting coating.

27. The apparatus of claim 1, wherein the thick-film electrode comprises at least one member selected from the group consisting of metals, inorganic dopants, organic dopants, nucleic acids, catalytic surface modifiers, enzymatic surface modifiers, and permselective film coatings.

28. The apparatus of claim 1, further comprising at least one cavity in fluidic connection with the inlet end of the separation channel.

29. The apparatus of claim 28, further comprising a buffer cavity and sample cavity in fluidic connection with the inlet end of the separation channel.

30. The apparatus of claim 28, further comprising a reaction cavity in fluidic connection with the inlet end of the separation channel.

31. The apparatus of claim 28, further comprising a plurality of separation channels with the inlet ends thereof in fluidic connection with at least one cavity.

32. The apparatus of claim 1, further comprising at least one cavity in fluidic connection with the outlet end of the separation channel.

33. The apparatus of claim 1, comprising a plurality of separation channels and a plurality of thick-film electrodes.

34. The apparatus of claim 1, wherein both the first substrate and the second substrate are substantially planar, and the second substrate is at an angle to the first substrate.

35. The apparatus of claim 34, wherein the second substrate is perpendicular to the first substrate.

36. The apparatus of claim 1, wherein both the first substrate and the second substrate are substantially planar and parallel to each other.

37. The apparatus of claim 36, wherein the second substrate forms a seal for at least a portion of the separation channel of the first substrate.

38. The apparatus of claim 1, wherein the separation channel further comprises separation media.

39. A method for detecting an analyte, comprising the steps of:
   providing a substrate with a microfluidic channel disposed thereon, the microfluidic channel having an inlet end and an outlet end transiting an exterior edge of the first substrate;
   introducing the analyte in the inlet end of the microfluidic channel;
   transporting the analyte in a fluid solution through the microfluidic channel to the outlet end;
   contacting the solution containing the analyte with a thick-film electrode disposed on a second substrate and in fluidic connection with the outlet end of the microfluidic channel;
   providing electrical contact to the thick-film electrode; and
   analyzing the analyte at the thick-film electrode by electrochemical detection.

40. The method of claim 39 further comprising the step of:
   providing electrical contact to at least one counter electrode in fluidic contact with the thick-film electrode.

41. The method of claim 39 further comprising the steps of:
   providing at least one reactant for the analyte; and
   mixing the at least one reactant and the analyte prior to analyzing the analyte at the thick-film electrode by electrochemical detection.

42. The method of claim 39, wherein the microfluidic channel comprises a microfluidic separation channel.

43. The method of claim 39, wherein transporting the analyte in a fluid solution through the microfluidic channel is by electrokinetic fluid transport.

44. The method of claim 43, wherein the electrokinetic fluid transport is capillary electrophoresis.

45. The method of claim 39, wherein transporting the analyte in a fluid solution through the microfluidic channel comprises at least one method selected from the group consisting of electrical, mechanical, centrifugal, magnetic, pneumatic, pressure-activated, and vacuum-activated fluid transport.

46. The method of claim 39, wherein analyzing the analyte at the thick-film electrode by electrochemical detection comprises amperometric detection.

47. The method of claim 46, wherein the amperometric detection comprises at least one member selected from the group consisting of fixed potential and potential-step amperometric detection.

48. The method of claim 39, wherein analyzing the analyte at the thick-film electrode by electrochemical detection comprises at least one member selected from the group consisting of stripping potentiometry and voltammetric detection.

49. The method of claim 39, wherein the thick-film electrode is a screen-printed electrode.

50. The method of claim 39, wherein the microfluidic channel has an average bore diameter of from about 1 μm to about 300 μm.

51. The method of claim 50, wherein the microfluidic channel has an average bore diameter of from about 20 μm to about 120 μm.

52. The method of claim 39, wherein the thick-film electrode has a thickness of from about 1 μm to about 100 μm.

53. The method of claim 52, wherein the thickness of the thick-film electrode is between about 8 μm and 30 μm.

54. The method of claim 39, wherein the distance between the thick-film electrode in fluidic connection with the outlet end of the microfluidic channel and the microfluidic channel is fixed.

55. The method of claim 54, wherein the distance between the thick-film electrode and the outlet end of the microfluidic channel is from about 1 μm to about 500 μm.

56. The method of claim 55, wherein the distance is between about 50 μm and about 100 μm.

57. The method of claim 39, wherein the thick-film electrode comprises a carbon ink electrode.

58. The method of claim 39, wherein the thick-film electrode comprises a metal conducting coating.

59. The method of claim 39, wherein the thick-film electrode comprises at least one member selected from the group consisting of metals, inorganic dopants, organic dopants, nucleic acids, catalytic surface modifiers, enzymatic surface modifiers, and permselective film coatings.

60. The method of claim 39, wherein the fluid solution comprises a buffer solution.

61. The method of claim 39, wherein the analyte comprises at least one member selected from the group consisting of nitroaromatic compounds, catecholamines, hydrazine compounds, phenolic compounds, enzyme-specific compounds, amino acids, nucleic acids, metal ions and anions.

62. The method of claim 61, wherein said nucleic acids are selected from the group consisting of DNA, scDNA, ssDNA, dsDNA, RNA and tRNA.

63. The method of claim 39, wherein the microfluidic channel further comprises separation media.

64. An apparatus for conducting a microfluidic process and analysis, said apparatus comprising:
a first substantially planar substrate having at least one defined edge;
at least one elongated separation channel in the first substrate, the separation channel having an inlet end and an outlet terminating at a defined edge;
a second substrate with at least one thick-film electrode for analyte detection disposed thereon, the second substrate being removably positionable at a non-zero angle with respect to the first substrate and the thick-film electrode being in fluidic connection with the outlet end of the separation channel.

65. The apparatus of claim 64, wherein the second substrate is removably positionable perpendicular to the first substrate.

66. The apparatus of claim 64, further comprising a holder for holding the first substrate in a removably positionable position with respect to the second substrate.

67. The apparatus of claim 66, wherein the first substrate is attached to the holder and the second substrate is removably attached to the holder.

68. The apparatus of claim 66, wherein the first substrate and the second substrate are removably attached to the holder.

69. The apparatus of claim 64, further comprising a conductive system in fluidic connection with each end of the separation channel for application of a separation voltage.

70. The apparatus of claim 64, further comprising an electrokinetic fluid transport system.

71. The apparatus of claim 64, further comprising a fluidic transport means for transport of fluid through the separation channel comprising at least one means elected from the group consisting of electrical, mechanical, centrifugal, magnetic, pneumatic, pressure-activated, and vacuum-activated fluid transport.

72. The apparatus of claim 64, further comprising at least one reference electrode in fluidic connection with the thick-film electrode.

73. The apparatus of claim 64, wherein the thick-film electrode is a screen-printed electrode.

74. The apparatus of claim 64, wherein the thick-film electrode has a thickness of from about 1 μm to about 100 μm.

75. The apparatus of claim 74, wherein the thickness of the thick-film electrode is between about 8 μm and 30 μm.

76. The apparatus of claim 64, wherein the second substrate is adjustably positionable relative to the first substrate such that the distance between the thick-film electrode and the outlet of the separation channel is variably and adjustably positionable.

77. The apparatus of claim 76, wherein the distance between the thick-film electrode and the outlet of the separation channel is from about 1 μm to about 500 μm.

78. The apparatus of claim 77, wherein the distance is between about 50 μm and about 100 μm.

79. The apparatus of claim 64, wherein the thick-film electrode comprises a carbon ink electrode.

80. The apparatus of claim 64, wherein the thick-film electrode comprises a metal conducting coating.

81. The apparatus of claim 64, wherein the thick-film electrode comprises at least one member selected from the group consisting of metals, inorganic dopants, organic dopants, nucleic acids, catalytic surface modifiers, enzymatic surface modifiers, and permselective film coatings.

82. The apparatus of claim 64, comprising a plurality of separation channels and a plurality of thick-film electrodes.

* * * * *